US007342131B2

(12) United States Patent
Xiang et al.

(10) Patent No.: US 7,342,131 B2
(45) Date of Patent: *Mar. 11, 2008

(54) LEVODOPA PRODRUGS, AND COMPOSITIONS AND USES THEREOF

(75) Inventors: Jia-Ning Xiang, Palo Alto, CA (US); Mark A. Gallop, Los Altos, CA (US); Cindy X. Zhou, Palo Alto, CA (US); Mark Nguyen, San Jose, CA (US); Xuedong Dai, San Jose, CA (US); Jianhua Li, Sunnyvale, CA (US); Kenneth C. Cundy, Redwood City, CA (US); Nelson L. Jumbe, Mountain View, CA (US)

(73) Assignee: XenoPort, Inc., Santa Clara, CA (US)

( * ) Notice: Subject to any disclaimer, the term of this patent is extended or adjusted under 35 U.S.C. 154(b) by 95 days.

This patent is subject to a terminal disclaimer.

(21) Appl. No.: 11/145,159

(22) Filed: Jun. 3, 2005

(65) Prior Publication Data

US 2005/0282891 A1 Dec. 22, 2005

Related U.S. Application Data

(60) Provisional application No. 60/577,087, filed on Jun. 4, 2004.

(51) Int. Cl.
C07C 233/00 (2006.01)
C07C 69/00 (2006.01)
(52) U.S. Cl. .................. 564/161; 564/192; 560/129
(58) Field of Classification Search ............ 560/8, 560/19, 24, 55; 562/405, 433, 465; 564/305, 564/363, 346

See application file for complete search history.

(56) References Cited

U.S. PATENT DOCUMENTS

| 3,811,444 | A |   | 5/1974  | Heller et al.    |         |
|-----------|---|---|---------|------------------|---------|
| 3,962,414 | A |   | 6/1976  | Michaels         |         |
| 3,992,518 | A |   | 11/1976 | Chien et al.     |         |
| 4,066,747 | A |   | 1/1978  | Capozza          |         |
| 4,070,347 | A |   | 1/1978  | Schmitt          |         |
| 4,079,038 | A |   | 3/1978  | Choi et al.      |         |
| 4,083,949 | A |   | 4/1978  | Benedikt         |         |
| 4,093,709 | A |   | 6/1978  | Choi et al.      |         |
| 4,134,991 | A | * | 1/1979  | Wermuth          | 514/533 |
| 4,311,706 | A |   | 1/1982  | Bodor et al.     |         |
| 4,663,349 | A |   | 5/1987  | Repta            |         |
| 4,771,073 | A |   | 9/1988  | Repta            |         |
| 4,826,875 | A |   | 5/1989  | Chiesi           |         |
| 4,873,263 | A |   | 10/1989 | Repta            |         |
| 4,966,915 | A |   | 10/1990 | Tsuchiya et al.  |         |
| 5,017,607 | A |   | 5/1991  | Chiesi           |         |
| 5,462,933 | A |   | 10/1995 | Kramer et al.    |         |
| 5,607,969 | A |   | 3/1997  | Milman et al.    |         |
| 5,827,819 | A | * | 10/1998 | Yatvin et al.    | 514/2   |
| 5,840,756 | A |   | 11/1998 | Cohen et al.     |         |

| 2002/0099041 | A1 | 7/2002 | Gallop et al.   |
|--------------|----|--------|-----------------|
| 2003/0158254 | A1 | 8/2003 | Zerangue et al. |

FOREIGN PATENT DOCUMENTS

| EP | 309 827 B1    |   | 1/1992 |
|----|---------------|---|--------|
| JP | 58024547      |   | 2/1983 |
| WO | 198604579     | * | 8/1986 |
| WO | WO 86/04579   |   | 8/1986 |
| WO | WO 88/01615   |   | 3/1988 |
| WO | WO 02/28882   |   | 4/2002 |

OTHER PUBLICATIONS

Garzon-Aburbeh et al., Journal of Medicinal Chemistry (1986), 29(5), 687-91.*
Goodman and Gilman's The Pharmacological Basis of Therapeutics, 8th ed. 1990. pp. 463-473.*
U.S. Appl. No. 11/145,280, filed Jun. 3, 2005, Xiang et al.
Fix et al., "A Comparison of Oral and Rectal Absorption of L-Dopa Esters in Rats and Mice," *Pharm. Res.*, 7(4):384-387 (1990).
Gennaro (Ed.), Title Page and Table of Contents, in : *Remington's Pharmaceutical Sciences*, 17th Edition, Mack Publishing Co., Easton, PA, 5 pages (1985).
Marrel et al., "L-DOPA esters as potential prodrugs," *Eur. J. Med. Chem. Chim. Ther.*, 5:459-465 (1985).
International Search Report and Written Opinion mailed Nov. 3, 2005, for Application No. PCT/US2005/019492, filed Jun. 3, 2005.
International Search Report and Written Opinion mailed Nov. 3, 2005, for Application No. PCT/US2005/019493, filed Jun. 3, 2005.
Bai. 1995, "pGlu-L-Dopa-Pro: A Tripeptide Prodrug Targeting the Intestinal Peptide Transporter for Absorption and Tissue Enzymes for Conversion," *Pharmaceutical Research*, 12(7): 1101-1104.
Bodor et al., 1977, "Improved Delivery through Biological Membranes. 4. Prodrugs of L-Dopa," *Journal of Medicinal Chemistry*, 20(11): 1435-1445.
Coleman et al., 1990, "Polymer reviews: A practical guide to polymer miscibility," *Polymer*, 31: 1187-1203.
Cooper et al., 1987, "L-Dopa esters as potential prodrugs: behavioural activity in experimental models of Parkinson's disease," *J. Pharm. Pharmacol.*, 39: 627-635.
Di Stefano et al., 2001, "Dimeric L-Dopa Derivatives as Potential Prodrugs," *Bioorganic & Medicinal Chemistry Letters*, 11: 1085-1088.
During et al., 1989, "Controlled Release of Dopamine from a Polymeric Brain Implant: In Vivo Characterization," *Ann. Neurol.*, 25(4): 351-356.
Felmeister, 1970, Chapter 86: Powders: Particle size reduction, classification, and measurement-mixing of powders—powders as a dosage form, pp. 1626-1628 from *Remington's Pharmaceutical Sciences, Fourteenth Edition*, Hoover (ed.), Mack Publishing Company, Easton, PA.
Fincher, 1968, "Particle Size of Drugs and Its Relationship to Absorption and Activity," *J. Pharm. Sci.*, 57(11): 1825-1835.

(Continued)

*Primary Examiner*—Karl Puttlitz
(74) *Attorney, Agent, or Firm*—Finnegan, Henderson, Farabow, Garrett & Dunner, L.L.P.

(57) ABSTRACT

Prodrugs of levodopa, methods of making prodrugs of levodopa, methods of using prodrugs of levodopa, and compositions of prodrugs of levodopa are disclosed.

45 Claims, No Drawings

OTHER PUBLICATIONS

Fix et al, 1989, "Short-Chain Alkyl Esters of L-Dopa as Prodrugs for Rectal Absorption," *Pharmaceutical Research*, 6(6): 501-505.

Garzon-Aburbeh et al., 1986, "A Lymphotropic Prodrug of L-Dopa: Synthesis, Pharmacological Properties, and Pharmacokinetic Behavior of 1,3-Dihexadecanoyl-2-[(S)-2-amino-3-(3,4-dihydroxyphenyl)propanoyl]propane-1,2,3-triol," *J. Med. Chem.* 29: 687-691.

Goodson, 1984, Chapter 6: Dental Applications, pp. 115-138 from *Medical Applications of Controlled Release*, vol. II: *Applications and Evaluation*, Langer and Wise (eds.), CRC Press, Inc., Boca Raton, FL.

Greene and Wuts (eds.), 1991, Title page, Preface, and Contents from *Protective Groups in Organic Synthesis, Second Edition*, John Wiley & Sons, Inc., New York.

Greene and Wuts (eds.), 1999, Title page, Prefaces, and Contents from *Protective Groups in Organic Synthesis, Third Edition*, John Wiley & Sons, Inc., New York.

Harrison et al. (eds.), 1971-1995, Title pages, Prefaces, and Contents from *Compendium of Synthetic Organic Methods*, vols. 1-8, John Wiley & Sons, Inc. New York.

Hisaka et al., 1990, "Absorption of a Novel Prodrug of L-Dopa, L-3-(Hydroxy-4-Pivaloyloxphenyl)alanine (NB-355): In Vitro and In Situ Studies," *Drug Metabolism and Disposition*, 18(5): 621-625.

Hoes and Feijen, 1989, The Application of Drug-Polymer Conjugates in Chemotherapy, pp. 57-109 from *Horizons in Biochemistry and Biophysics* vol. 9: *Drug Carrier Systems*, John Wiley & Sons, New York.

Howard et al., 1989, "Intracerebral drug delivery in rats with lesion-induced memory deficits," *J. Neurosurg.*, 71: 105-112.

Ishikura et al., 1995, "Drug delivery to the brain. DOPA prodrugs based on a ring-closure reaction to quaternary thiazolium compounds," *Int'l. Journal of Pharmaceutics*, 116: 51-63.

Juncos et al., 1987, "Levodopa methyl ester treatment of Parkinson's disease," *Neurology*, 37: 1242-1245.

King and Schwartz, 1985, Chapter 90: Oral Solid Dosage Forms, pp. 1603-1632 from *Pharmaceutical Sciences*, Mack Publishing Company, Easton, PA.

Langer, 1990, "New Methods of Drug Delivery," *Science*, 249: 1527-1533.

Langer and Peppas, 1983, "Chemical and Physical Structure of Polymers as Carriers for Controlled Release of Bioactive Agents: A Review," *JMS-Rev. Macromol. Chem. Phys.*, C23(1): 61-126.

Langer and Wise (eds.), 1984, Title page and Table of Contents from *Medical Applications of Controlled Release*, vol. I: *Classes of Systems* and vol. II: *Applications and Evaluation*, CRC Press, Inc., Boca Raton, FL.

Larock, 1999, Title Page and Contents from *Comprehensive Organic Transformations: A Guide to Functional Groups, Second Edition*, Wiley-VCH, New York.

Leong and Langer, 1987, "Polymeric controlled drug delivery," *Advanced Drug Delivery Reviews*, 1: 199-233.

Leppert et al., 1988, "The Effects of Carbidopa Dose and Time and Route of Administration on Systemic L-Dopa Levels in Rats," *Pharmaceutical Research*, 5(9): 587-591.

Levy et al., 1985, "Inhibition of Calcification of Bioprosthetic Heart Valves by Local Controlled-Release Diphosphonate," *Science*, 228: 190-192.

Linhardt, 1989, Chapter 2: Biodegradable Polymers for Controlled Release of Drugs, pp. 53-95 from *Controlled Release of Drugs: Polymers and Aggregate Systems*, M. Rosoff (ed.), VCH Publishers.

Lu and Yu, 1994, "Dimensionless presentation for drug release from a coated pure drug bead: 2. Experiment," *International Journal of Pharmaceutics*, 112: 117-124.

March, 1992, Title page and Contents from *Advanced Organic Chemistry: Reactions, Mechanisms, and Structure, Fourth Edition*, John Wiley & Sons, New York.

Roff et al. (eds.), 1971, Title Page, Preface, Acknowledgements, Contents, How to Use This Book, 1. List of Sections on Individual Polymers, and 2. List of Sections on Specific Properties and Related Information from *Handbook of Common Polymers: Fibres, Films, Plastics and Rubbers*, CRC Press, Cleveland, OH.

Sasahara et al., 1980, "Dosage Form Design for Improvement of Bioavailability of Levodopa II: Bioavailability of Marketed Levodopa Preparations in Dogs and Parkinsonian Patients," *Journal of Pharmaceutical Sciences*, 69(3): 261-265.

Saudek et al., 1989, "A Preliminary Trial of the Programmable Implantable Medication System for Insulin Delivery," *N. Engl. J. Med.*, 321: 574-579.

Sefton, 1987, "Implantable Pumps," *CRC Critical Reviews in Biomedical Engineering*, 14(3): 201-240.

Smith, 1994, Title Page and Contents from *Organic Synthesis*, McGraw-Hill, Inc., New York.

Smolen and Ball (eds.), 1984, Title Page and Contents from *Controlled Drug Bioavailability*, vol. 1: *Drug Product Design and Performance*, John Wiley & Sons, New York.

Verma et al., 2000, "Osmotically Controlled Oral Drug Delivery," *Drug Development and Industrial Pharmacy*, 26(7): 695-708.

Wang et al., 2002, "Preparation and Intestinal Absorption of L-Dopa-D-phenylglycine," *Journal of Food and Drug Analysis*, 10(2): 81-87.

Wang et al., 1995, "Synthesis and Pharmacological Activities of a Novel Tripeptide Mimetic Dopamine Prodrug," *Bioorganic & Medicinal Chemistry Letters*, 5(19): 2195-2198.

\* cited by examiner

LEVODOPA PRODRUGS, AND COMPOSITIONS AND USES THEREOF

This application claims benefit of U.S. Provisional Application No. 60/577,087 filed Jun. 4, 2004, which is incorporated by reference herein in its entirety.

Embodiments of the present invention are directed to prodrugs of levodopa, methods of making prodrugs of levodopa, methods of using prodrugs of levodopa, and compositions of prodrugs of levodopa.

Parkinson's disease is a disabling, progressive illness that affects one in 1,000 people and generally occurs in people over the age of 50 years. Patients with Parkinson's disease have a deficiency of the neurotransmitter dopamine in the brain as a result of the nigrostriatal pathway disruption caused by degeneration of the substantia nigra. Levodopa (L-dopa or L-3,4-dihydroxyphenylalanine), an immediate precursor of dopamine, is the most commonly prescribed drug for treatment of this disease.

Following oral administration, levodopa is rapidly absorbed via an amino acid transporter present in the upper small intestine. Due to the narrow distribution of this transporter system, the window available for levodopa absorption is limited and the extent of absorption can be dependent on the rate at which the drug passes through the upper gastrointestinal tract. Approximately 35% of the administered dose reaches the systemic circulation as intact levodopa after oral administration in patients (Sasahara, 1980, *J. Pharm. Sci.,* 69, 261). The absolute bioavailability of levodopa is dose-dependent, due to saturation of the active transport pathway. Plasma levels of levodopa must be carefully titrated for each patient to achieve the optimal therapeutic activity. If the concentration of levodopa is too low in plasma (and consequently in the brain) the patient can experience a return of the symptoms of Parkinson's disease (rigidity, tremor, bradykinesia). On the other hand, motor fluctuation can become a significant side effect if plasma drug levels are too high. Uncontrolled fluctuations in plasma levodopa levels can greatly contribute to the incidence of "on-off" fluctuations (dyskinesias). The most effective control of Parkinsonism is observed when plasma levels of levodopa are maintained in a narrow range, for example, by continuous intraduodenal infusion.

Once absorbed, levodopa is rapidly converted to dopamine by L-aromatic amino acid decarboxylase (AADC) in the peripheral tissues (e.g., intestines and liver). It has been known that intestinal metabolism of levodopa is the major source of first pass loss of the drug. In patients, only 1% of the administered dose reaches the central nervous system intact, following transport across the blood-brain barrier by the neutral amino acid transporter. For this reason, levodopa is normally co-administered with a drug designed to inhibit its peripheral decarboxylation such as carbidopa or benserazide. When administered with carbidopa, the plasma intact levodopa amount increases and thus more levodopa becomes available to be transported into the central nervous system where it is converted to dopamine. Carbidopa and benseraside themselves do not cross the blood-brain barrier to a significant extent, and therefore do not inhibit the required conversion of levodopa to dopamine in the brain.

The oral bioavailability of levodopa from conventional formulations of levodopa/carbidopa (e.g., Sinemet®) is 84-99% (Physician's Desk Reference). The half-life of levodopa in the plasma of patients is about 50 min when administered alone, or 1 to 2 hours when given with carbidopa. For this reason, the drug must be administered three or more times per day.

A formulation of levodopa/carbidopa (Sinemet® CR) intended to provide a controlled release of both drugs is commercially available. Sinemet® CR is designed for release of both levodopa and carbidopa over a 4-6 hour period. However, absorption of levodopa is limited to the small intestine and the resulting bioavailability of levodopa from Sinemet® CR is reduced relative to the immediate release product. In most cases, Sinemet® CR must also be given more than twice per day to achieve a therapeutic level of levodopa. Delayed and extended release formulations that release drug over periods of about 10-24 hours, and hence release much of the drug loading in the large intestine, have not been effective for delivering levodopa since levodopa is poorly absorbed from the large instestine. A simple enteric-coated formulation of levodopa led to increased gastrointestinal side effects (nausea) but did not improve absorption. A sustained release formulation of levodopa/carbidopa has been described that employs a swellable matrix (Geomatrix) delivery system to retain the drug in the stomach (Genta Jago product licensing information, June 1997). However, this formulation was designed to be bioequivalent to the commercially available Sinemet® CR formulation and therefore does not provide the desired goal of a once or twice per day dosing regimen.

The use of simple ester prodrugs of levodopa to improve the pharmacokinetics of the drug has been proposed (U.S. Pat. Nos. 5,017,607; 4,826,875; 4,873,263; 4,771,073; 4,663,349; 4,311,706; Japanese Patent No. JP58024547; Juncos et al., 1987, *Neurology,* 37:1242; and Cooper et al., 1987, *J. Pharm. Phanmacol.,* 39:627-635). An oral formulation of levodopa methyl ester (Levomet®, CHF 1301) has been described (Chiesi Pharmaceuticals). The ethyl ester of levodopa (TV-1203) is under clinical investigation as a potential therapy for Parkinsonism when co-administered with carbidopa (U.S. Pat. No. 5,607,969). A sustained cellulose formulation of levodopa ethyl ester in a mixture of hydroxypropylmethyl cellulose, hydroxypropyl cellulose, and a carboxyvinyl polymer has been described (U.S. Pat. No. 5,840,756). However, oral administration of this formulation to healthy adults pretreated with carbidopa produced a plasma levodopa terminal half-life of only 2 hr, comparable to that of Sinemet® CR.

A pivaloyl ester of levodopa (NB-355) has been described (European Patent No. 0 309 827). Following oral administration of NB-355, no rapid increase or elimination of levodopa was observed and duration time was prolonged, while levels of levodopa were low. The potential for using ester prodrugs of levodopa to enhance rectal absorption of the drug has been described (U.S. Pat. Nos. 4,663,349; 4,771,073; and 4,873,263). Notably, the absorption of simple alkyl esters of levodopa has been shown to be greater following rectal absorption than following oral dosing (Fix, et al., *Pharm. Res.,* 1989, 6:501-5; Fix, et al., *Pharm. Res.,* 1990, 4:384-7). This effect is attributed to the decreased abundance of esterases in the large intestine relative to the small intestine. Therefore, selective delivery of a prodrug of levodopa to the large intestine in a sustained release formulation might be expected to provide a greater oral bioavailability and a prolonged exposure to the drug.

A series of glycolic acid ester containing prodrugs of levodopa has been described (Wermuth, U.S. Pat. No. 4,134, 991). Lipid conjugates of levodopa to facilitate the entry of drug into cells and tissues have also been described (Yatvin, U.S. Pat. No. 5,827,819).

The half-life of levodopa is prolonged and its bioavailability increased by the co-administration of carbidopa. Both drugs have relatively short half-lives of less than about 2 hours. Any method of sustained delivery of levodopa to the systemic circulation would therefore require a sufficient level of carbidopa to continuously inhibit peripheral decarboxylation of levodopa. In order to avoid the need for frequent (more than twice per day) dosing of levodopa and carbidopa, it is desirable to deliver both levodopa and carbidopa (or prodrug thereof) in a sustained manner. It has been proposed that rectal co-administration of an AADC inhibitor such as carbidopa with an ester prodrug of levodopa would be possible as a means to decrease metabolic clearance of levodopa (U.S. Pat. Nos. 4,663,349; 4,771,073; and 4,873,263). However, studies in rats have since indicated that absorption of carbidopa following rectal administration is poor (Leppert et al., 1988, *Pharm. Res.*, 5:587-591).

Thus, the development of levodopa prodrugs that can be efficiently absorbed throughout the gastrointestinal tract, including the colon, and reduce first-pass metabolism of levodopa, is highly desirable.

Certain embodiments of the present invention are related to prodrugs of levodopa, which are capable of undergoing absorption across the intestinal epithelium via active and/or passive transport.

Certain embodiments of the present invention are related to prodrugs of levodopa which are capable of undergoing absorption across the intestinal epithelium via active transport mechanisms, and more particularly to levodopa prodrugs that are substrates for organic cation transporters expressed throughout the gastrointestinal tract.

The human gastrointestinal tract includes the small intestine and the large intestine. The human small intestine is a convoluted tube about twenty feet in length between the stomach and large intestine. The small intestine is subdivided into the duodenum, the jejunum, and the ileum. The large intestine is about 5 feet in length and runs from the ileum to the anus. The large intestine is divided into the caecum, colon, and the rectum. The colon is divided into four parts including the ascending, traverse, descending, and the sigmoid flexure. In general, an orally ingested compound resides about 1 to 6 hours in the stomach, about 2 to 7 hours in the small intestine, and about 8 to 18 hours in the colon. Thus, the greatest period of time for sustained release of a compound occurs when the compound is passing through the colon.

Certain active transporter proteins are known to be expressed throughout the gastrointestinal tract. An active transporter refers to a membrane-bound protein that recognizes a substrate and affects the entry of the substrate into, or exit from a cell by carrier-mediated transport or receptor-mediated transport. Active transport includes movement of molecules across cellular membranes that is directly or indirectly dependent on an energy mediated process, such as for example is driven by ATP hydrolysis or an ion gradient, that occurs by facilitated diffusion mediated by interaction with specific transporter proteins, and that occurs through a modulated solute channel. For example, organic cation transporters such as OCTN1 and OCTN2 are expressed in the epithelial cells lining a human colon as well as in the small intestine.

Thus, levodopa prodrugs that act as substrates for one or more organic cation transporter(s) can exhibit increased active transporter-mediated absorption during the extended period of time that the compound passes through the gastrointestinal tract. Increased absorption and in particular colonic absorption of levodopa prodrug can result in the increased systemic bioavailability of the compound over an extended period of time. Systemic bioavailability refers to the rate and extent of systemic exposure to a drug or an active metabolite thereof as reflected in the integrated systemic blood concentration over a period of time, also referred to as "area under the curve."

In certain embodiments, levodopa prodrugs are capable of absorption over a significant length of the gastrointestinal tract, including the large intestine, and in particular the colon. Such prodrugs can be incorporated into conventional sustained release formulations including osmotic delivery devices to provide sustained systemic exposure to levodopa upon oral administration to a patient. Many of such prodrugs can be coadministered with a decarboxylase inhibitor such as carbidopa or benserazide, or a prodrug of thereof, and in some embodiments also formulated as sustained release compositions, with the carbidopa/levodopa prodrug compositions or benserazide/levodopa prodrug compositions together providing prolonged exposure to levodopa at levels necessary to affect sustained anti-Parkinson's therapy. Certain embodiments include carbidopa prodrugs that can block first-pass levodopa decarboxylation within the intestinal enterocytes either as the intact carbidopa prodrug, or through generation of carbidopa from carbidopa prodrug cleavage within the enterocytes and which can be cleaved to provide carbidopa in the systemic circulation. Decarboxylase inhibitor/levodopa prodrug or decarboxylase inhibitor prodrug/levodopa prodrug sustained release compositions can also be administered together with inhibitors of catechol O-methyltransferase (COMT) such as entacapone or tolcapone, to further block peripheral clearance of levodopa.

Among levodopa prodrugs contemplated by certain embodiments are prodrugs in which the carboxyl moiety of levodopa is masked to form a carboxyl ester, which can be cleaved in vivo to release the parent drug (e.g., levodopa). Optionally, the catechol moieties of levodopa can additionally be masked with promoieties, these promoieties being cleaved either before or after cleavage of the carboxyl ester promoiety.

Suitable catechol protecting moieties in the aforementioned prodrugs can be elaborated by functionalizing one or more of the phenolic hydroxy groups via acylation or other appropriate methods. The corresponding esters, carbonates, and (hemi)acetals/(hemi)ketals can be cleaved in vivo to regenerate the catechol moieties of the parent drug.

Certain embodiments of the present invention provide at least one levodopa prodrug of Formula (I)

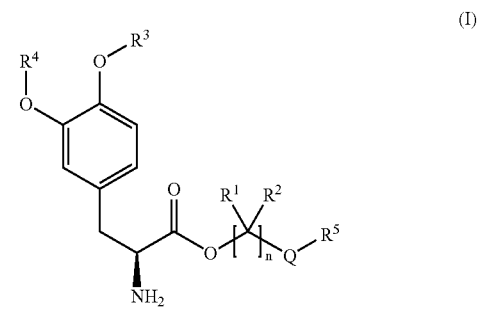

(I)

a stereoisomer thereof, an enantiomer thereof, a pharmaceutically acceptable salt thereof, a hydrate thereof, or a solvate of any of the foregoing, wherein Q is selected from —X—CO—, and —CO—X—;

X is selected from —O—, and —NR$^6$—;

n is an integer from 2 to 4;

each $R^1$ and $R^2$ is independently selected from hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, halo, heteroalkyl, substituted heteroalkyl, heteroaryl, substituted heteroaryl, heteroarylalkyl, and substituted heteroarylalkyl;

$R^3$ and $R^4$ are independently selected from hydrogen, —C(O)OR$^7$, —C(O)R$^7$, and —(CR$^8$R$^9$)OC(O)R$^{10}$;

$R^5$ is selected from hydrogen, alkyl, substituted alkyl, aryl, substituted aryl, arylalkyl, substituted arylalkyl, cycloalkyl, substituted cycloalkyl, heteroalkyl, substituted heteroalkyl, cycloheteroalkyl, substituted cycloheteroalkyl, heteroaryl, substituted heteroaryl, heteroarylalkyl, and substituted heteroarylalkyl; and when Q is —X—CO—, $R^5$ is further selected from alkoxy, substituted alkoxy, cycloalkoxy, and substituted cycloalkoxy;

$R^6$ is selected from hydrogen, alkyl, substituted alkyl, aryl, substituted aryl, arylalkyl, and substituted arylalkyl;

$R^7$ is selected from alkyl, substituted alkyl, cycloalkyl, substituted cycloalkyl, cycloheteroalkyl, substituted cycloheteroalkyl, aryl, substituted aryl, arylalkyl, substituted arylalkyl, heteroaryl, substituted heteroaryl, heteroarylalkyl, and substituted heteroarylalkyl;

$R^8$ and $R^9$ are independently selected from hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroaryl, substituted heteroaryl, heteroarylalkyl, and substituted heteroarylalkyl, or optionally, $R^8$ and $R^9$ together with the carbon atom to which $R^8$ and $R^9$ are attached form a cycloalkyl, substituted cycloalkyl, cycloheteroalkyl or substituted cycloheteroalkyl ring; and $R^{10}$ is selected from hydrogen, alkyl, substituted alkyl, aryl, substituted aryl, arylalkyl, substituted arylalkyl, cycloalkyl, substituted cycloalkyl, heteroalkyl, substituted heteroalkyl, cycloheteroalkyl, substituted cycloheteroalkyl, heteroaryl, substituted heteroaryl, heteroarylalkyl, and substituted heteroarylalkyl;

with the proviso that the compound of Formula (I) is not derived from 1,3-dihexadecanoylpropane-1,2,3-triol.

Certain embodiments of the present invention provide compositions comprising at least one levodopa prodrug. In certain embodiments, the compositions comprise at least one levodopa prodrug, or an enantiomer and stereoisomer of any of the foregoing, or a pharmaceutically acceptable salt thereof, a hydrate thereof, or a solvate of any of the foregoing and a pharmaceutically acceptable diluent, carrier, excipient and/or adjuvant of any of the foregoing. The choice of diluent, carrier, excipient and/or adjuvant can depend upon, among other factors, the desired mode of administration.

Certain embodiments of the present invention provide methods of treating Parkinson's disease. The methods comprise co-administering to a patient in need of such treatment a therapeutically effective amount of at least one of the following: (i) at least one levodopa prodrug; (ii) at least one levodopa prodrug and at least one decarboxylase inhibitor; (iii) at least one levodopa prodrug and at least one decarboxylase inhibitor prodrug; (iv) a stereoisomer or an enantiomer of any of the foregoing; and (v) a pharmaceutically acceptable salt thereof, a hydrate thereof or a solvate of any of the foregoing. In certain embodiments, the composition is administered to a patient using a sustained-release dosage form.

In certain embodiments, the at least one levodopa prodrug can be released from the dosage form, e.g., an orally administered dosage form, over a sufficient period of time to provide prolonged therapeutic concentrations of levodopa in the blood of a patient enabling administration of the dosage form on only a once or twice per day basis. In certain embodiments, the at least one levodopa prodrug can maintain a therapeutic or prophylactic blood concentration of levodopa or levodopa prodrug in the systemic circulation of a patient following oral administration of a levodopa prodrug over a period of at least 4 hours, in certain embodiments, over a period of at least 8 hours, and in certain embodiments, over a period of at least 12 hours. Similarly, a decarboxylase inhibitor (e.g., carbidopa, benserazide or prodrug thereof), when dosed with a levodopa prodrug, can be released from the dosage form or device immediately after the dosage form is administered, over a period of hours up to, for example, 16 hours after administration of the dosage form with greater than 75% of the decarboxylase inhibitor released, or coextensively released with the release of the levodopa prodrug.

The oral sustained release dosage forms used with certain embodiments can take any form as long as the release characteristics and pharmacokinetic profiles above are satisfied. For example, the dosage form can be in the form of an osmotic dosage form, a prodrug-releasing polymer, prodrug-releasing tiny timed-release pills, prodrug-releasing lipids, prodrug-releasing waxes and/or prodrug-releasing beads.

Certain embodiments of the present invention provide compositions for treating Parkinson's disease in a patient in need of such treatment. The compositions comprise a therapeutically effective amount of at least one of the following: (i) levodopa prodrug; (ii) levodopa prodrug and decarboxylase inhibitor; (iii) levodopa prodrug and decarboxylase inhibitor prodrug; (iv) a stereoisomer or an enantiomer of any of the foregoing; and (v) a pharmaceutically acceptable salt thereof, a hydrate thereof or a solvate of any of the foregoing. In certain embodiments, the composition further comprises a sustained-release dosage form.

Certain embodiments of the present invention methods for making levodopa prodrugs, compositions comprising at least one levodopa prodrug, methods of using levodopa prodrugs, and methods of using compositions comprising at least one levodopa prodrug for treating Parkinson's disease.

Specific Embodiments

Definitions

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the properties sought to be obtained. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the embodiments are approximations, the numerical values set forth in the specific examples are reported as precisely as possible. Any numerical values, however, inherently contain certain errors necessarily resulting form the standard deviation found in their respective testing measurements.

To the extent the definitions of terms in the publications, patents, and patent applications incorporated herein by reference are not the same as the definitions set forth in this specification, the definitions in this specification control for the entire specification, including the claims. Any other definitions in the publications, patents, and patent applications incorporated herein by reference that are not explicitly provided in this specification apply only to the embodiments discussed in the publications, patents, and patent applications incorporated herein by reference.

"Compounds" refers to compounds encompassed by generic formulae disclosed herein, any subgenus of those generic formulae, and any specific compounds within those generic or subgeneric formulae. The compounds can be a specific specie, a subgenus or larger genus identified either by their chemical structure and/or chemical name. Further, compounds also include substitutions or modifications of any of such species, subgenuses or genuses, which are set forth herein. When the chemical structure and chemical name conflict, the chemical structure is determinative of the identity of the compound. The compounds can contain one or more chiral centers and/or double bonds and therefore, can exist as stereoisomers, such as double-bond isomers (i.e., geometric isomers), enantiomers or diastereomers. Accordingly, the chemical structures within the scope of the specification encompass all possible enantiomers and stereoisomers of the illustrated compounds including the stereoisomerically pure form (e.g., geometrically pure, enantiomerically pure or diastereomerically pure) and enantiomeric and stereoisomeric mixtures. Further, when partial structures of the compounds are illustrated, asterisks indicate the point of attachment of the partial structure to the rest of the molecule. Enantiomeric and stereoisomeric mixtures can be resolved into their component enantiomers or stereoisomers using separation techniques or chiral synthesis techniques well known to the skilled artisan.

"Alkyl" refers to a saturated or unsaturated, branched, straight-chain or cyclic monovalent hydrocarbon group derived by the removal of one hydrogen atom from a single carbon atom of a parent alkane, alkene or alkyne. Typical alkyl groups include, but are not limited to, methyl; ethyls such as ethanyl, ethenyl, ethynyl; propyls such as propan-1-yl, propan-2-yl, cyclopropan-1-yl, prop-1-en-1-yl, prop-1-en-2-yl, prop-2-en-2-yl (allyl), cycloprop-1-en-1-yl; cycloprop-2-en-1-yl, prop-1-yn-1-yl, prop-2-yn-1-yl; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl; and the like.

The term "alkyl" is specifically intended to include groups having any degree or level of saturation, i.e., groups having exclusively single carbon-carbon bonds, groups having one or more double carbon-carbon bonds, groups having one or more triple carbon-carbon bonds and groups having mixtures of single, double and triple carbon-carbon bonds. Where a specific level of saturation is intended, the expressions "alkanyl," "alkenyl," and "alkynyl" are used. In certain embodiments, an alkyl group comprises from 1 to 20 carbon atoms.

"Alkanyl" refers to a saturated branched, straight-chain or cyclic alkyl group derived by the removal of one hydrogen atom from a single carbon atom of a parent alkane. Typical alkanyl groups include, but are not limited to, methanyl; ethanyl; propanyls such as propan-1-yl, propan-2-yl (isopropyl), cyclopropan-1-yl; butanyls such as butan-1-yl, butan-2-yl (sec-butyl), 2-methyl-propan-1-yl (isobutyl), 2-methyl-propan-2-yl (t-butyl), cyclobutan-1-yl; and the like.

"Alkenyl" refers to an unsaturated branched, straight-chain or cyclic alkyl group having at least one carbon-carbon double bond derived by the removal of one hydrogen atom from a single carbon atom of a parent alkene. The group can be in either the cis or trans conformation about the double bond(s). Typical alkenyl groups include, but are not limited to, ethenyl; propenyls such as prop-1-en-1-yl, prop-1-en-2-yl, prop-2-en-1-yl (allyl), prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, cyclobut-1-en-1yl, cyclobut-1-en-3-yl, cyclobuta-1,3-dien-1-yl; and the like.

"Alkynyl" refers to an unsaturated branched, straight-chain or cyclic alkyl group having at least one carbon-carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl; butynyls such as but-1-yn-1-yl, but-1-yn-3-yl, but-3-yn-1-yl; and the like.

"Alkylene" refers to a saturated or unsaturated, branched, straight-chain or cyclic divalent hydrocarbon group derived by the removal of two hydrogen atoms from a parent alkane, alkene or alkyne. Typical alkylene groups include, but are not limited to methylene, ethylene, propylene, butylenes, and the like.

"Acyl" refers to a radical —C(O)R, where R is hydrogen, alkyl, cycloalkyl, cycloheteroalkyl, aryl, arylalkyl, heteroalkyl, heteroaryl, heteroarylalkyl as defined herein. Representative examples include, but are not limited to, formyl, acetyl, cylcohexylcarbonyl, cyclohexylmethylcarbonyl, benzoyl, benzylcarbonyl, and the like.

"Alkoxy" refers to a radical —OR where R represents an alkyl or cycloalkyl group as defined herein. Representative examples include, but are not limited to, methoxy, ethoxy, propoxy, butoxy, cyclohexyloxy, and the like.

"Aryl" refers to a monovalent aromatic hydrocarbon group derived by the removal of one hydrogen atom from a single carbon atom of a parent aromatic ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like. In certain embodiments, an aryl group comprises from 6 to 20 carbon atoms.

"Arylene" refers to a divalent aromatic hydrocarbon group derived by removal of two hydrogen atoms from a parent aromatic ring system.

"Arylalkyl" refers to an acyclic alkyl group in which one of the hydrogen atoms bonded to a carbon atom, typically a terminal or $sp^3$ carbon atom, is replaced with an aryl group. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl, and the like. Where specific alkyl moieties are intended, the nomenclature arylalkanyl, arylalkenyl, and/or arylalkynyl is used. In certain embodiments, an arylalkyl group is ($C_6$-$C_{30}$) arylalkyl, e.g., the alkanyl, alkenyl or alkynyl moiety of the arylalkyl group is ($C_1$-$C_{10}$) and the aryl moiety is ($C_5$-$C_{20}$).

"Arylalkylene" refers to a divalent acyclic alkyl group in which one of the hydrogen atoms bonded to a carbon atom, typically a terminal or $sp^3$ carbon atom is replaced with an aryl group.

"Arylalkyloxy" refers to an —O-arylalkyl group where arylalkyl is as defined herein.

"Cyano" refers to the radical —CN.

"Cycloalkyl" refers to a saturated or unsaturated cyclic alkyl group. Where a specific level of saturation is intended, the nomenclature "cycloalkanyl" or "cycloalkenyl" is used. Typical cycloalkyl groups include, but are not limited to, groups derived from cyclopropane, cyclobutane, cyclopentane, cyclohexane, and the like. In a certain embodiment, the cycloalkyl group is ($C_3$-$C_{10}$) cycloalkyl, or in certain embodiments ($C_3$-$C_6$) cycloalkyl.

"Cycloheteroalkyl" refers to a saturated or unsaturated cyclic alkyl group in which one or more carbon atoms (and any associated hydrogen atoms) are independently replaced with the same or different heteroatom. Typical heteroatoms to replace the carbon atom(s) include, but are not limited to, N, P, O, S, and Si. Where a specific level of saturation is intended, the nomenclature "cycloheteroalkanyl" or "cycloheteroalkenyl" is used. Typical cycloheteroalkyl groups include, but are not limited to, groups derived from epoxides, imidazolidine, morpholine, piperazine, piperidine, pyrazolidine, pyrrolidine, quinuclidine, and the like.

"Compound of Formula (I) derived from 1,3-dihexadecanoylpropane-1,2,3-triol" refers to a moiety of structural formula:

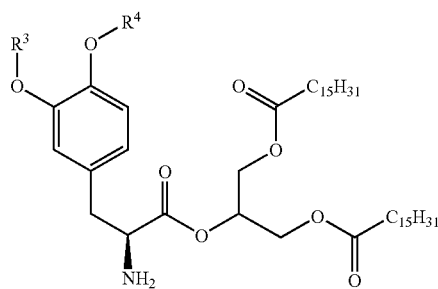

"Halo" refers to fluoro, chloro, bromo, or iodo.

"Heteroalkyloxy" refers to an —O-heteroalkyl group where heteroalkyl is as defined herein.

"Heteroalkyl, Heteroalkanyl, Heteroalkenyl, Heteroalkynyl" refer to alkyl, alkanyl, alkenyl, and alkynyl groups, respectively, in which one or more of the carbon atoms (and any associated hydrogen atoms) are each independently replaced with the same or different heteroatomic groups. Typical heteroatomic groups include, but are not limited to, —O—, —S—, —O—O—, —S—S—, —O—S—, —NR'—, =N—N=, —N=N—, —N=N—NR'—, —PH—, —P(O)$_2$—, —O—P(O)$_2$—, —S(O)—, —S(O)$_2$—, —SnH$_2$—, and the like, wherein R' is hydrogen, alkyl, substituted alkyl, cycloalkyl, substituted cycloalkyl, aryl or substituted aryl.

"Heteroaryl" refers to a monovalent heteroaromatic group derived by the removal of one hydrogen atom from a single atom of a parent heteroaromatic ring system. Typical heteroaryl groups include, but are not limited to, groups derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. In certain embodiments, the heteroaryl group is between 5-20 membered heteroaryl, and in other embodiments is between 5-10 membered heteroaryl. In certain embodiments, heteroaryl groups are those derived from thiophene, pyrrole, benzothiophene, benzofuran, indole, pyridine, quinoline, imidazole, oxazole, and pyrazine.

"Heteroaryloxycarbonyl" refers to a radical —(O)—OR where R is heteroaryl as defined herein.

"Heteroarylalkyl" refers to an acyclic alkyl group in which one of the hydrogen atoms bonded to a carbon atom, typically a terminal or $sp^3$ carbon atom, is replaced with a heteroaryl group. Where specific alkyl moieties are intended, the nomenclature heteroarylalkanyl, heteroarylalkenyl, and/or heteroarylalkynyl is used. In certain embodiments, the heteroarylalkyl group is a 6-30 membered heteroarylalkyl, e.g., the alkanyl, alkenyl or alkynyl moiety of the heteroarylalkyl is 1-10 membered and the heteroaryl moiety is a 5-20-membered heteroaryl.

"Leaving group" has the meaning conventionally associated with it in synthetic organic chemistry, i.e., an atom or a group capable of being displaced by a nucleophile and includes halo (such as chloro, bromo, and iodo), acyloxy (e.g., acetoxy, and benzoyloxy), mesyloxy, tosyloxy, trifluoromethanesulfonyloxy, aryloxy (e.g., 2,4-dinitrophenoxy), methoxy, N,O-dimethylhydroxylamino, and the like.

"Pharmaceutically acceptable" refers to approved or approvable by a regulatory agency of the Federal or a state government or listed in the U.S. Pharmacopeia or other generally recognized pharmacopeia for use in animals, and more particularly in humans.

"Pharmaceutically acceptable salt" refers to a salt of a compound that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo [2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, N-methylglucamine, dicyclohexylamine, and the like.

"Pharmaceutically acceptable vehicle" refers to a diluent, adjuvant, excipient or carrier with which a compound is administered.

"Extended release" refers to dosage forms that provide for the delayed, slowed over a period of time, continuous, discontinuous, or sustained release of a compound or composition.

"Patient" includes mammals and humans. The terms "human" and "patient" are used interchangeably herein.

"Prodrug" refers to a derivative of a drug molecule that requires one or more transformations, e.g., metabolism of the prodrug within the patient's body to cause the active drug to be formed. Prodrugs can be (though not necessarily) pharmacologically inactive until converted to the parent drug.

"Promoiety" refers to a group that is covalently attached to an active molecule that is potentially cleavable in vivo by enzymatic or non-enzymatic means. A promoiety can be, for example, a protecting group used to mask a functional group, a group that acts as a substrate for one or more active or passive transport mechanisms, or a group that acts to impart or enhance a certain property to the molecule, such as, for example, solubility.

"Protecting group" refers to a grouping of atoms that when attached to a reactive group in a molecule masks, reduces or prevents that reactivity. Examples of protecting groups can be found in Green et al., "Protective Groups in Organic Chemistry," (Wiley, 2$^{nd}$ ed. 1991) and Harrison et al., "Compendium of Synthetic Organic Methods," Vols. 1-8 (John Wiley and Sons, 1971-1996). Representative amino protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("SES"), trityl and substituted trityl groups, allyloxycarbonyl, 9-fluorenylmethyloxycarbonyl ("FMOC"), nitro-veratryloxycarbonyl ("NVOC"), and the like. Representative hydroxy protecting groups include, but are not limited to, those where the hydroxy group is either acylated or alkylated such as benzyl, and trityl ethers as well as alkyl ethers, tetrahydropyranyl ethers, trialkylsilyl ethers, and allyl ethers.

"Substituted" refers to a group in which one or more hydrogen atoms are each independently replaced with the same or different substituent(s). Typical substituents include, but are not limited to, —X, —R$^{33}$, —O$^{31}$, =O, —OR$^{33}$, —SR$^{33}$, —S$^{31}$, =S, —NR$^{33}$R$^{34}$, =NR$^{33}$, —CX$_3$, —CF$_3$, —CN, —OCN, —SCN, —NO, —NO$_2$, =N$_2$, —N$_3$, —S(O)$_2$O$^-$, —S(O)$_2$OH, —S(O)$_2$R$^{33}$, —OS(O$_2$)O$^-$, —OS(O)$_2$R$^{33}$, —P(O)(O$^-$)$_2$, —P(O)(OR$^{33}$)(O$^-$), —OP(O)(OR$^{33}$)(OR$^{34}$), —C(O)R$^{33}$, —C(S)R$^{33}$, —C(O)OR$^{33}$, —C(O)NR$^{33}$R$^{34}$, —C(O)O$^{31}$, —C(S)OR$^{33}$, —NR$^{35}$C(O)NR$^{33}$R$^{34}$, —NR$^{35}$C(S)NR$^{33}$R$^{34}$, —NR$^{35}$C(NR$^{33}$)NR$^{33}$R$^{34}$ and —C(NR$^{33}$)NR$^{33}$R$^{34}$, where each X is independently a halogen; each R$^{33}$ and R$^{34}$ are independently hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl, substituted heteroarylalkyl, —NR$^{35}$R$^{36}$, —(O) R$^{35}$ or —S(O)$_2$R$^{35}$ or optionally R$^{33}$ and R$^{34}$ together with the atom to which R$^{33}$ and R$^{34}$ are attached form a cycloheteroalkyl or substituted cycloheteroalkyl ring; and R$^{35}$ and R$^{36}$ are independently hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl or substituted heteroarylalkyl. In certain embodiments, a substituent group is selected from halo, —CN, —NO$_2$, —OH, C$_{1-6}$ alkyl, and C$_{1-6}$ alkoxy. In certain embodiments, a substituent group is selected from halo, —OH, C$_{1-3}$ alkyl, and C$_{1-3}$ alkoxy.

"Treating" or "treatment" of any disease or disorder refers to arresting or ameliorating a disease or disorder, reducing the risk of acquiring a disease or disorder, reducing the development of a disease or disorder or at least one of the clinical symptoms of the disease or disorder, or reducing the risk of developing a disease or disorder or at least one of the clinical symptoms of a disease or disorder. "Treating" or "treatment" also refers to inhibiting the disease or disorder, either physically, (e.g., stabilization of a discernible symptom), physiologically, (e.g., stabilization of a physical parameter), or both, and inhibiting at least one physical parameter which may not be discernible to the patient. Further, "treating" or "treatment" refers to delaying the onset of the disease or disorder or at least symptoms thereof in a patient which may be exposed to or predisposed to a disease or disorder even though that patient does not yet experience or display symptoms of the disease or disorder.

"Therapeutically effective amount" refers to the amount of a compound that, when administered to a patient for treating a disease or disorder, is sufficient to affect such treatment for the disease or disorder. The "therapeutically effective amount" will vary depending on the compound, the disease or disorder and its severity and the age and weight of the patient to be treated.

"Cleave" refers to breakage of chemical bonds and is not limited to chemical or enzymatic reactions or mechanisms unless clearly indicated by the context.

Reference will now be made in detail to certain embodiments.

Compounds

Compounds include levodopa prodrugs to which promoieties have been attached. In certain embodiments, compounds include levodopa derivatives of Formula (I):

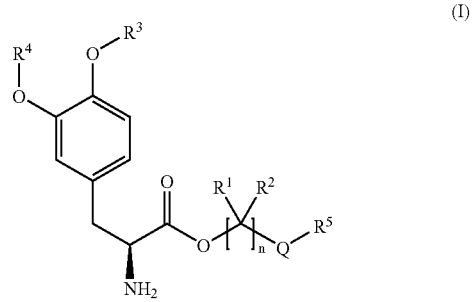

(I)

a stereoisomer thereof, an enantiomer thereof, a pharmaceutically acceptable salt thereof, a hydrate thereof, or a solvate of any of the foregoing, wherein Q is selected from —X—CO—, and —CO—X—;

X is selected from —O—, and —NR$^6$—;

n is an integer from 2 to 4;

each R$^1$ and R$^2$ is independently selected from hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, halo, heteroalkyl, substituted heteroalkyl, heteroaryl, substituted heteroaryl, heteroarylalkyl, and substituted heteroarylalkyl;

$R^3$ and $R^4$ are independently selected from hydrogen, —C(O)OR$^7$, —C(O)R$^7$, and —(CR$^8$R$^9$)OC(O)R$^{10}$;

$R^5$ is selected from hydrogen, alkyl, substituted alkyl, aryl, substituted aryl, arylalkyl, substituted arylalkyl, cycloalkyl, substituted cycloalkyl, heteroalkyl, substituted heteroalkyl, cycloheteroalkyl, substituted cycloheteroalkyl, heteroaryl, substituted heteroaryl, heteroarylalkyl, and substituted heteroarylalkyl; and when Q is —X—CO—, $R^5$ is further selected from alkoxy, substituted alkoxy, cycloalkoxy, and substituted cycloalkoxy;

$R^6$ is selected from hydrogen, alkyl, substituted alkyl, aryl, substituted aryl, arylalkyl, and substituted arylalkyl;

$R^7$ is selected from alkyl, substituted alkyl, cycloalkyl, substituted cycloalkyl, cycloheteroalkyl, substituted cycloheteroalkyl, aryl, substituted aryl, arylalkyl, substituted arylalkyl, heteroaryl, substituted heteroaryl, heteroarylalkyl, and substituted heteroarylalkyl;

$R^8$ and $R^9$ are independently selected from hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroaryl, substituted heteroaryl, heteroarylalkyl, and substituted heteroarylalkyl, or optionally, $R^8$ and $R^9$ together with the carbon atom to which $R^{16}$ and $R^{17}$ are attached form a cycloalkyl, substituted cycloalkyl, cycloheteroalkyl or substituted cycloheteroalkyl ring; and $R^{10}$ is selected from hydrogen, alkyl, substituted alkyl, aryl, substituted aryl, arylalkyl, substituted arylalkyl, cycloalkyl, substituted cycloalkyl, heteroalkyl, substituted heteroalkyl, cycloheteroalkyl, substituted cycloheteroalkyl, heteroaryl, substituted heteroaryl, heteroarylalkyl, and substituted heteroarylalkyl;

with the proviso that the compound of Formula (I) is not derived from 1,3-dihexadecanoylpropane-1,2,3-triol.

In certain embodiments of a compound of Formula I, Q is —X—CO—. In certain embodiments of a compound of Formula I, wherein Q is —X—CO—, X is O. In certain embodiments of a compound of Formula I, wherein Q is —X—CO—, X is —NR$^6$—.

In certain embodiments of a compound of Formula I, Q is —CO—X—. In certain embodiments of a compound of Formula I, wherein Q is —CO—X, X is O. In certain embodiments of a compound of Formula I, wherein Q is —CO—X, X is —NR$^6$—.

In certain embodiments of a compound of Formula I, each $R^1$ and $R^2$ is independently selected from hydrogen, —OH, $C_{1-6}$ alkyl, and substituted $C_{1-6}$ alkyl.

In certain embodiments of a compound of Formula I, each $R^1$ and $R^2$ is independently selected from hydrogen, —OH, $C_{1-3}$ alkyl, and substituted $C_{1-3}$ alkyl.

In certain embodiments of a compound of Formula I, $R^5$ is selected from alkanyl, substituted alkanyl, alkenyl, substituted alkenyl, arylalkanyl, substituted arylalkanyl, arylalkenyl, substituted arylalkenyl, cycloalkanyl, substituted cycloalkanyl, cycloheteroalkanyl, substituted cycloheteroalkanyl, heteroarylalkanyl, and substituted heteroarylalkanyl. In certain embodiments of a compound of Formula I, $R^5$ is selected from methyl, ethyl, propyl, isopropyl, butyl, isobutyl, sec-butyl, tert-butyl, pentyl, hexyl, cyclopropyl, cyclobutyl, cyclopentyl, cyclohexyl, benzyl, phenethyl, and styryl, where the aryl ring of the benzyl or styryl group is optionally substituted with one or more substituents selected from halo, —CN, —NO$_2$, —OH, $C_{1-6}$ alkyl, and $C_{1-6}$ alkoxy.

In certain embodiments of a compound of Formula I, $R^5$ is selected from aryl, substituted aryl, heteroaryl, and substituted heteroaryl. In certain embodiments of a compound of Formula I, $R^5$ is selected from $C_{5-8}$ aryl, and substituted $C_{5-8}$ aryl substituted with one or more substituents selected from halo, —CN, —NO$_2$, —OH, $C_{1-6}$ alkyl, and $C_{1-6}$ alkoxy. In certain embodiments of a compound of Formula I, $R^5$ is selected from phenyl and pyridyl which are optionally substituted with halo, —OH, $C_{1-3}$ alkyl, and $C_{1-3}$ alkoxy.

In certain embodiments of a compound of Formula I, each $R^1$ and $R^2$ is independently selected from hydrogen, alkanyl, substituted alkanyl, arylalkanyl, substituted arylalkanyl, cycloalkanyl, substituted cycloalkanyl, cycloheteroalkanyl, substituted cycloheteroalkanyl, halo, heteroalkanyl, substituted heteroalkanyl, heteroarylalkanyl, and substituted heteroarylalkanyl. In certain embodiments of a compound of Formula I, each $R^1$ and $R^2$ is independently selected from hydrogen, methyl, ethyl, propyl, isopropyl, butyl, isobutyl, sec-butyl, tert-butyl, cyclopropyl, cyclobutyl, cyclopentyl, cyclohexyl, and benzyl.

In certain embodiments of a compound of Formula I, each $R^1$ and $R^2$ is independently selected from hydrogen, aryl, substituted aryl, heteroaryl, and substituted heteroaryl. In certain embodiments of a compound of Formula I, each $R^1$ and $R^2$ is independently selected from hydrogen and phenyl, wherein the phenyl group is optionally substituted with one or more substituents selected from halo, —CN, —NO$_2$, —OH, $C_{1-6}$ alkyl, and $C_{1-6}$ alkoxy.

In certain embodiments of a compound of Formula I, each $R^1$ and $R^2$ is independently selected from hydrogen, —OH, $C_{1-4}$ alkyl, and substituted $C_{1-4}$ alkyl.

In certain embodiments of a compound of Formula I, each $R^1$ and $R^2$ is independently selected from hydrogen, —OH, $C_{1-3}$ alkyl, and substituted $C_{1-3}$ alkyl.

In certain embodiments of a compound of Formula I, each $R^1$ and $R^2$ is hydrogen.

In certain embodiments of a compound of Formula I, $R^6$ is selected from hydrogen and $C_{1-6}$ alkyl. In certain embodiments, $R^6$ is hydrogen, and in certain embodiments, $R^6$ is methyl.

In certain embodiments of a compound of Formula I, $R^3$ and $R^4$ are independently selected from hydrogen, —C(O)OR$^7$, and —C(O)R$^7$.

In certain embodiments of a compound of Formula I, $R^7$ is selected from alkanyl, substituted alkanyl, cycloalkanyl, substituted cycloalkanyl, arylalkanyl, substituted arylalkanyl, heteroarylalkanyl, and substituted heteroarylalkanyl. In certain embodiments, $R^7$ is selected from methyl, ethyl, propyl, isopropyl, butyl, isobutyl, secbutyl, tert-butyl, cyclopropyl, cyclobutyl, cyclopentyl, cyclohexyl and benzyl, wherein the aryl ring of the benzyl group is optionally substituted with one or more substituents selected from halo, —CN, —NO$_2$, —OH, $C_{1-6}$ alkyl, and $C_{1-6}$ alkoxy.

In certain embodiments of a compound of Formula I, $R^7$ is selected from aryl, substituted aryl, heteroaryl, and substituted heteroaryl. In certain embodiments, $R^7$ is selected from $C_{5-8}$ aryl, substituted $C_{5-8}$ aryl, $C_{6-10}$ arylalkyl, and substituted $C_{6-10}$ arylalkyl. In certain embodiments, $R^7$ is selected from phenyl, pyridyl, furyl, and thienyl, the aromatic rings of which are optionally substituted with one or more substituents selected from halo, —CN, —NO$_2$, —OH, $C_{1-6}$ alkyl, and $C_{1-6}$ alkoxy.

In certain embodiments of a compound of Formula I, $R^3$ and $R^4$ are independently selected from hydrogen and $—CR^8R^9)OC(O)R^{10}$.

In certain embodiments of a compound of Formula I, $R^{10}$ is selected from hydrogen, $C_{1-10}$ alkyl, substituted $C_{1-10}$ alkyl, $C_{5-8}$ aryl, substituted $C_{5-8}$ aryl, $C_{1-15}$ alkoxy, and substituted $C_{1-5}$ alkoxy.

In certain embodiments of a compound of Formula I, $R^8$ and $R^9$ are independently selected from hydrogen, $C_{1-16}$ alky, substituted $C_{1-16}$ alkyl, $C_{5-8}$ aryl, substituted $C_{5-8}$ aryl, $C_{6-10}$ arylalkyl, and substituted $C_{6-10}$ arylalkyl.

In certain other embodiments, compounds include levodopa prodrugs of Formula (II):

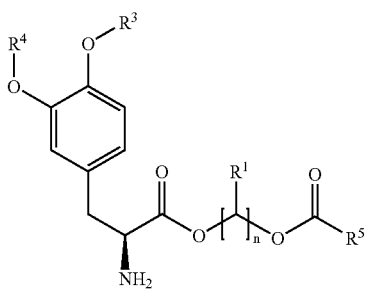

(II)

a stereoisomer thereof, an enantiomer thereof, a pharmaceutically acceptable salt thereof, a hydrate thereof, or a solvate of any of the foregoing, wherein n is an integer from 2 to 4, $R^1$ is selected from hydrogen, a straight chain $C_{1-3}$ alkyl, and a branched $C_{1-3}$ alkyl, and $R^5$ is selected from phenyl, and substituted phenyl wherein one or more of the substituents is selected from halo, $—CN$, $—NO_2$, $—OH$, $C_{1-6}$ alkyl, and $C_{1-6}$ alkoxy. Certain embodiments of a compound of Formula (II) have the following structures:

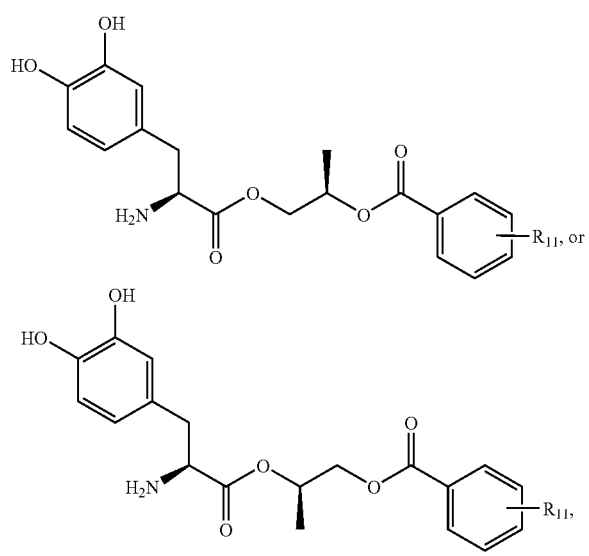

wherein $R^{11}$ is selected from hydrogen, halo, $—CN$, $—NO_2$, $—OH$, $C_{1-6}$ alkyl, and $C_{1-6}$ alkoxy.

In certain embodiments of a compound of Formula I, the compound is selected from:

2-Phenylcarbonyloxyethyl (2S)-2-amino-3-(3,4-dihydroxyphenyl)propanoate;

2-(4-Fluorophenylcarbonyloxy)ethyl (2S)-2-amino-3-(3,4-dihydroxyphenyl)propanoate;

3-Phenylcarbonyloxypropyl (2S)-2-amino-3-(3,4-dihydroxyphenyl)propanoate;

3-(4-Fluorophenylcarbonyloxy)propyl (2S)-2-amino-3-(3,4-dihydroxyphenyl)propanoate;

2-Acetyloxyethyl (2S)-2-amino-3-(3,4-dihydroxyphenyl)propanoate;

(2R)-2-Phenylcarbonyloxypropyl (2S)-2-amino-3-(3,4-dihydroxyphenyl)propanoate;

(2S)-2-Phenylcarbonyloxypropyl (2S)-2-amino-3-(3,4-dihydroxyphenyl)propanoate;

(2R)-2-(4-Fluorophenylcarbonyloxy)propyl (2S)-2-amino-3-(3,4-dihydroxyphenyl)propanoate;

(2S)-2-(4-Fluorophenylcarbonyloxy)propyl (2S)-2-amino-3-(3,4-dihydroxyphenyl)propanoate;

(1R)-1-Methyl-2-phenylcarbonyloxyethyl (2S)-2-amino-3-(3,4-dihydroxyphenyl)propanoate;

(1S)-1-Methyl-2-phenylcarbonyloxyethyl (2S)-2-amino-3-(3,4-dihydroxyphenyl)propanoate;

(1R)-1-Methyl-2-(4-fluorophenylcarbonyloxy)ethyl (2S)-2-amino-3-(3,4-dihydroxyphenyl)propanoate;

(1S)-1-Methyl-2-(4-fluorophenylcarbonyloxy)ethyl (2S)-2-amino-3-(3,4-dihydroxyphenyl)propanoate;

(1R,2R)-1-Methyl-2-phenylcarbonyloxypropyl (2S)-2-amino-3-(3,4-dihydroxyphenyl)propanoate;

(1S,2S)-1-Methyl-2-phenylcarbonyloxypropyl (2S)-2-amino-3-(3,4-dihydroxyphenyl)propanoate;

(1R,2R)-1-Methyl-2-(4-fluorophenylcarbonyloxy)propyl (2S)-2-amino-3-(3,4-dihydroxyphenyl)propanoate;

(1S,2S)-1-Methyl-2-(4-fluorophenylcarbonyloxy)propyl (2S)-2-amino-3-(3,4-dihydroxyphenyl)propanoate;

3-(4-Methoxyphenylcarbonyloxy)propyl (2S)-2-amino-3-(3,4-dihydroxyphenyl)propanoate;

3-(2-Hydroxyphenylcarbonyloxy)propyl (2S)-2-amino-3-(3,4-dihydroxyphenyl)propanoate;

3-(4-Hydroxyphenylcarbonyloxy)propyl (2S)-2-amino-3-(3,4-dihydroxyphenyl)propanoate;

2-Hydroxy-3-phenylcarbonyloxypropyl (2S)-2-amino-3-(3,4-dihydroxyphenyl)propanoate;

(2R)-2-(2-Hydroxyphenylcarbonyloxy)propyl (2S)-2-amino-3-(3,4-dihydroxyphenyl)propanoate;

(2R)-2-(4-Hydroxyphenylcarbonyloxy)propyl (2S)-2-amino-3-(3,4-dihydroxyphenyl)propanoate;

(2R)-2-(4-Methoxyphenylcarbonyloxy)propyl (2S)-2-amino-3-(3,4-dihydroxyphenyl)propanoate;

2-[(2-Hydroxyphenyl)carbonylamino]ethyl (2S)-2-amino-3-(3,4-dihydroxyphenyl)propanoate;

2(R)-(3-Pyridylcarbonyloxy)propyl (2S)-2-amino-3-(3,4-dihydroxyphenyl)propanoate;

2(S)-(3-Pyridylcarbonyloxy)propyl (2S)-2-amino-3-(3,4-dihydroxyphenyl)propanoate;

2(R)-(4-Pyridylcarbonyloxy)propyl (2S)-2-amino-3-(3,4-dihydroxyphenyl)propanoate;

2(S)-(4-Pyridylcarbonyloxy)propyl (2S)-2-amino-3-(3,4-dihydroxyphenyl)propanoate;

2(R)-(2-Ethoxy-3-pyridylcarbonyloxy)propyl (2S)-2-amino-3-(3,4-dihydroxyphenyl)propanoate;

2(S)-(2-Ethoxy-3-pyridylcarbonyloxy)propyl (2S)-2-amino-3-(3,4-dihydroxyphenyl)propanoate;

2(R)-(2-Methyl-5-pyridylcarbonyloxy)propyl (2S)-2-amino-3-(3,4-dihydroxyphenyl)propanoate;

2(S)-(2-Methyl-5-pyridylcarbonyloxy)propyl (2S)-2-amino-3-(3,4-dihydroxyphenyl)propanoate; and pharmaceutically acceptable salts thereof.

In certain embodiments of the above compounds, the pharmaceutically acceptable salt is the hydrochloride salt.

Synthesis of Certain Compounds

Embodiments of levodopa prodrugs can be prepared by methods well known in the art.

In certain embodiments the compounds can be prepared from readily available starting materials using the following general methods and procedures. It will be appreciated that where typical or preferred process conditions (i.e., reaction temperatures, times, mole ratios of reactants, solvents, pressures) are given, other process conditions can also be used unless otherwise stated. Optimum reaction conditions can vary with the particular reactants or solvent used, but such conditions can be determined by one skilled in the art by routine optimization procedures.

Additionally, as will be apparent to those skilled in the art, conventional protecting groups can be used to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and G. M. Wuts, *Protecting Groups in Organic Synthesis* and references cited therein.

Furthermore, in certain embodiments, the levodopa prodrugs can contain one or more chiral centers. Accordingly, such compounds can be prepared or isolated as pure stereoisomers, i.e., as individual enantiomers or diastereomers, or as stereoisomer-enriched mixtures. All such stereoisomers (and enriched mixtures) are included within the scope of the embodiments, unless otherwise indicated. Pure stereoisomers (or enriched mixtures) can be prepared using, for example, optically active starting materials or stereoselective reagents well known in the art. Alternatively, racemic mixtures of such compounds can be separated using, for example, chiral column chromatography, chiral resolving agents and the like.

In certain embodiments, levodopa prodrugs can be prepared by methods well known in the art (see Greene et al., *Protective Groups in Organic Synthesis*, Third Edition, John Wiley & Sons, 1999, and references cited therein; Larock, *Comprehensive Organic Transformations*, John Wiley & Sons, Second Edition, 1999; March, *Advanced Organic Chemistry*, John Wiley & Sons, Fourth Edition, 1992; Smith, *Organic Synthesis*, John Wiley & Sons, 1994; U.S. Pat. Nos. 4,966,915; 5,462,933. The disclosures of these references are herein incorporated by reference.

Some of the preparative methods can be found in Gallop et al. U.S. Patent Publication U.S. 2002/0099041 and Gallop et al. International Publication WO 02/28882.

A compound of Formula I can be prepared as illustrated in Scheme 1 below. Reacting Boc-protected levodopa (2) with a halide of Formula (3) in the presence of an appropriate base such as alkali metal bicarbonate or carbonate followed by hydrolysis of the Boc protecting group under acidic conditions affords a compound of Formula (I).

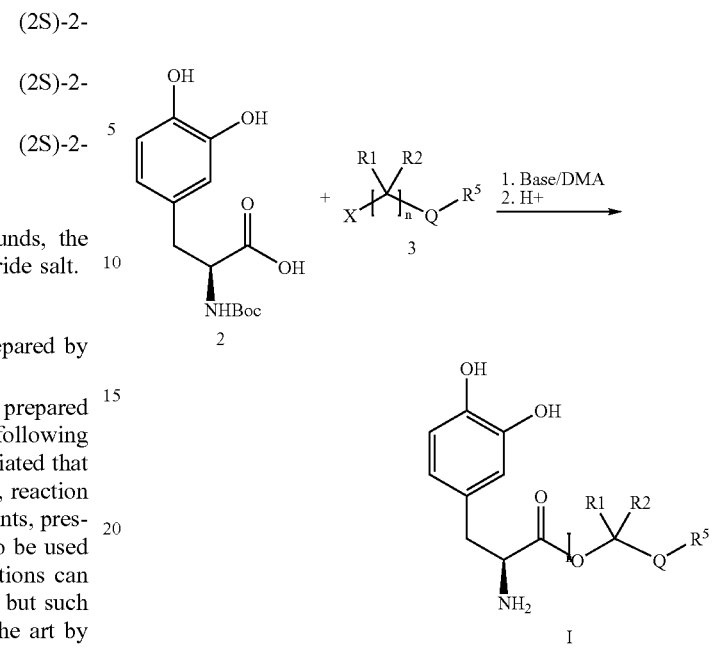

Alternatively, reacting an appropriately protected levodopa derivative (4) with an alcohol (5) under standard coupling conditions (Scheme 2) followed by removal of the protecting groups provides a compound of Formula (I).

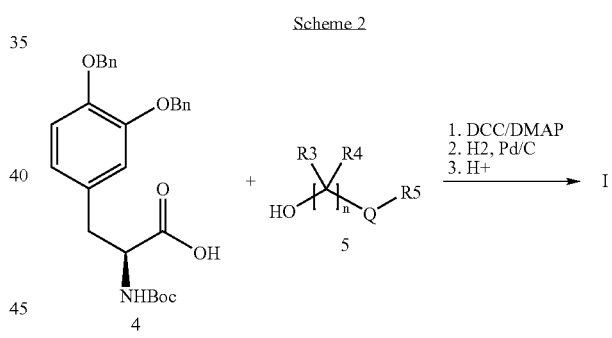

As shown in Scheme 3, an epoxide of Formula (6) can react with an acid of Formula (7) in the presence of a phase transfer reagent such as tetrabutylammonium bromide in an appropriate solvent (e.g., acetonitrile, toluene etc.) at an appropriate elevated temperature such as 50° C. to afford an alcohol of Formula (8), a compound of Formula (5), wherein Q is —X—C(O) and X is O.

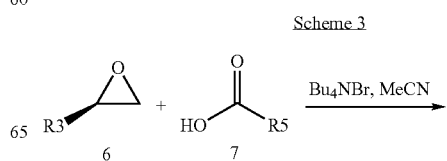

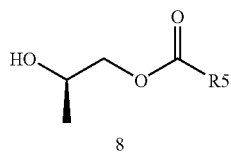

Alternatively, a hydroxyamine HO(CR$^1$R$^2$)$_n$NHR$^6$ (11) can be coupled with acid of Formula (7) to provide a compound of Formula (5), wherein Q is —XC(O) and X is —NR$^6$.

Alternatively, a diol of Formula (9) can be converted to a compound of Formula (10), which is further be coupled with a levodopa derivative of Formula (4) to provide a silyl ether of Formula (11). Reacting a silyl ether of Formula (11) with hydrogen fluoride affords an alcohol of Formula (12). Coupling of an alcohol of Formula (12) with an acid of Formula (7) under appropriate conditions (e.g., DCC/DMAP/DCM) followed by removal of the protecting groups under conditions described above provides a compound of Formula I (Scheme 4).

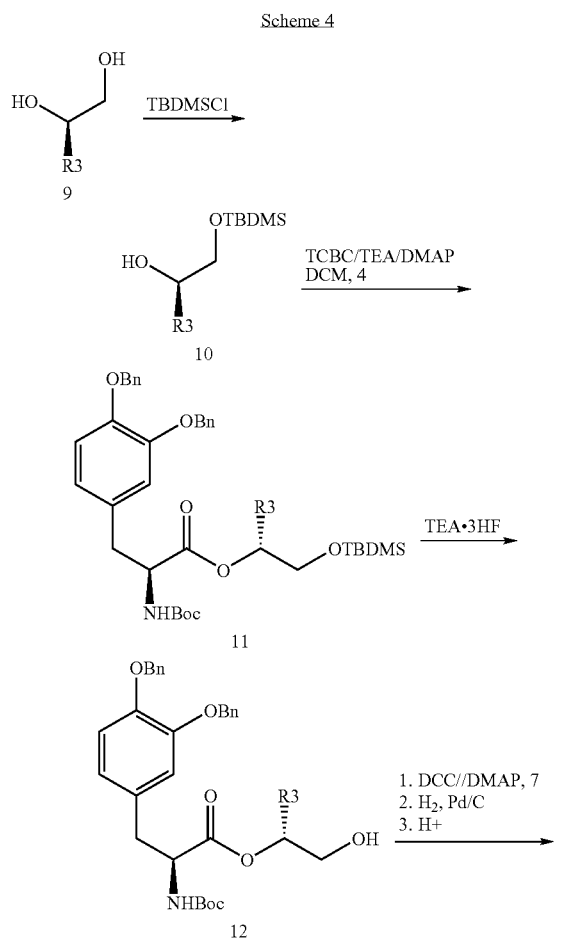

With appropriate manipulation and protection of the chemical functionalities, synthesis of the remaining compounds of Formula (I) is accomplished by methods analogous to those described above and in the experimental section.

Therapeutic Uses of Certain Compounds

In accordance with certain embodiments, levodopa prodrugs are precursors of dopamine. Thus, the levodopa prodrugs of Formula (I) can be administered to a patient, such as a human, to treat Parkinson's disease. In certain embodiments, at least one levodopa prodrug can be coadministered with another therapeutic agent or drug, such as a decarboxylase inhibitor, or a prodrug thereof, which can act as a protectant to inhibit or prevent premature decarboxylation of the levodopa prodrug and/or the levodopa metabolite.

The levodopa prodrugs can be delivered from the same dosage form as the decarboxylase inhibitor, or from a different dosage form. The levodopa prodrugs can be administered at the same time as, prior to, or subsequent to, the administration of a decarboxylase inhibitor. The levodopa prodrugs, together with a decarboxylase inhibitor or decarboxylase inhibitor prodrug or derivative, can be administered to a patient, such as a human, to treat Parkinson's disease.

Certain embodiments of compounds and compositions comprising at least one levodopa prodrug together with at least one decarboxylase inhibitor or at least one decarboxylase inhibitor prodrug or derivative can be advantageously used in human medicine. As disclosed herein, in certain embodiments, the compounds and compositions are useful for the treatment of Parkinson's disease. When used to treat Parkinson's disease, levodopa prodrugs can be administered or applied in combination with a decarboxylase inhibitor such as carbidopa and/or a carbidopa prodrug, or benserazide and/or a benserazide prodrug. Additionally, the therapeutic effectiveness of the above combinations can be further enhanced by co-administration of another pharmaceutically active agent such as a catechol oxygen methyl transferase (COMT) inhibitor. Further, in certain embodiments, the levodopa prodrugs, can be administered to a patient, such as a human, together with (i) a decarboxylase inhibitor such as carbidopa, benserazide or a prodrug thereof, and (ii) a pharmaceutically active agent such as a catechol oxygen methyl transferase (COMT) inhibitor or prodrug thereof, to treat Parkinson's disease.

The levodopa prodrugs disclosed herein are particularly adapted for oral administion, although they can also be administered by any other convenient route, such as for example, injection, infusion, inhalation, transdermal, absorption through epithelial or mucosal membranes (e.g., oral, rectal and/or intestinal mucosa).

In certain embodiments, the compounds and/or compositions provide levodopa and levodopa prodrugs upon in vivo administration to a patient. The promoiety or promoieties of the levodopa prodrugs are currently believed to be cleaved either chemically and/or enzymatically. One or more enzymes, such as cholesterases, present in the stomach, intestinal lumen, intestinal tissue, blood, liver, brain or any other suitable tissue of a mammal can enzymatically cleave the promoiety or promoieties of the compounds and/or compositions. The mechanism of cleavage is not important to the embodiments.

The promoiety or promoieties of certain embodiments of the compounds and/or compositions can be designed to be cleaved after absorption by the gastrointestinal tract, for example in intestinal tissue, blood, liver or other suitable tissue of a mammal. In this situation, levodopa prodrugs can be absorbed into the systemic circulation from the small and large intestines either by active transport, passive diffusion or by both active and passive processes. In certain embodiments, levodopa prodrugs are actively transported across the intestinal endothelium by organic cation transporters expressed throughout the gastrointestinal tract including the small intestine and colon. Certain compounds and/or compositions of levodopa prodrugs can be administered as sustained release systems. In certain embodiments, the compounds can be delivered by oral sustained release administration. In some embodiments, the compounds can be administered twice per day, in certain embodiments, once per day, and in certain embodiments at intervals greater than once per day.

Certain levodopa prodrugs can be useful in treating Parkinsonism by administration of one or more of the levodopa prodrugs together with a decarboxylase inhibitor such as carbidopa or a prodrug of carbidopa, in certain embodiments by the oral route, to a mammalian subject in need of the treatment. In a human subject weighing 70 kg, a levodopa prodrug can be administered at a dose having an equivalent weight of levodopa ranging from 10 mg to 10 g per day, and in certain embodiments, an equivalent weight of levodopa ranging from 100 mg to 3 g per day. The dose can be adjusted by one skilled in the art based on several factors, e.g. the body weight and/or condition of the subject treated, the dose of the decarboxylase inhibitor or prodrug of a decarboxylase inhibitor being administered, the severity of the Parkinson's disease, and the incidence of side effects, the manner of administration and the judgment of the prescribing physician. Dosage ranges can be determined by methods known to those skilled in the art.

The levodopa prodrugs can be assayed in vitro and in vivo, for the desired therapeutic or prophylactic activity prior to use in humans. For example, in vitro assays can be used to determine whether administration of a specific levodopa prodrug is a substrate of a transporter protein, including organic cation transporters such as OCTN1 and OCTN2. Examples of certain assay methods applicable to analyzing the ability of a specfic levodopa prodrug to act as a substrate for a transporter protein are disclosed in Zerangue et al. U.S. Appl. Publication 2003/0158254. In vitro assays can also be used to determine whether administraton of a specific levodopa prodrug is therapeutically effective. Levodopa prodrugs can also be demonstrated to be effective and safe using animal model systems.

In certain embodiments, a therapeutically effective dose of a levodopa prodrug can provide therapeutic benefit without causing substantial toxicity. Toxicity of levodopa prodrugs can be determined using standard pharmaceutical procedures and can be ascertained by the skilled artisan. The dose ratio between toxic and therapeutic effect is the therapeutic index. Certain levodopa prodrugs can exhibit particularly high therapeutic indices in treating diseases and disorders such as Parkinson's disease. The dosage of a levodopa prodrug can be within a range of circulating concentrations that include a therapeutically effective amount of levodopa prodrug with little or no toxicity.

In addition to the use of the levodopa prodrugs and compositions comprising levodopa prodrugs of the present disclosure for treating Parkinson's disease, in certain embodiments the prodrugs and compositions of the present disclosure can also be useful for treating other dopamine-related diseases. Dopamine-related diseases can be characterized by either insufficient or excessive functional dopaminergic activity in the central nervous system. Examples of other dopamine-related diseases include, but are not limited to, affective disorders such as depression and attention deficit disorder, psychotic disorders such as schizophrenia and manic depression, cognitive impairment disorders, movement disorders such as restless legs syndrome, periodic limb movement disorders, tardive dyskinesia, hypertension, Huntington's disease, and Tourette's syndrome, addictive disorders, congestive heart failure, and excessive daytime sleepiness. For the treatment of these diseases, a levodopa prodrug can be coadministered with an additional active agent. Therapeutically effective doses for treating dopamine-related diseases can be determined by the methods disclosed herein for the treatment of Parkinson's disease and by methods known in the art.

Formulations of Certain Compounds

In some embodiments, levodopa prodrugs can be incorporated into pharmaceutical compositions to be administered orally. Oral administration of such pharmaceutical compositons can result in uptake of the levodopa prodrugs throughout the intestine and entry into the systemic circulation. Such compositions can be prepared in a manner well known in the pharmaceutical art and comprise at least one levodopa prodrug. The present compositions can include a therapeutically effective amount of at least one levodopa prodrug, in some embodiments, in purified form, together with a decarboxylase inhibitor such as carbidopa, benserazide or a prodrug thereof, and a suitable amount of a pharmaceutically acceptable vehicle, so as to provide an approprate form for administration to a patient.

Certain embodiments also include compositions that comprise, as the active ingredient, at least one of the levodopa prodrugs associated with pharmaceutically acceptable excipients, carriers, diluents and/or adjuvants. In forming the compositions, the active ingredient can be mixed with an excipient, diluted by a diluent or enclosed within a carrier, which can be in the form of a capsule, sachet, paper or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, and syrups containing, for example, up to 90% by weight of the active compound using, for example, soft and hard gelatin capsules.

In preparing a composition, it can be useful to mill the active compound to provide an appropriate particle size prior to combining with other ingredients. For example, if the active compound is substantially insoluble, the active compound can be milled to a particle size of less than 200 mesh. If the active compound is substantially water soluble, the particle size of the active compound can be adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The compositions can additionally include lubricating agents such as talc, magnesium stearate, and mineral oil, wetting agents, emulsifying and suspending agents, preserving agents such as methyl- and propylhydroxy-benzoates, sweetening agents, pH adjusting and buffering agents, toxicity adjusting agents, flavoring agents, and the like. The compositions can be formulated so as to provide quick, sustained or delayed release of the active ingredient after administration to the patient by employing procedures known in the art.

A composition can be formulated in unit dosage form, each dosage comprising an equivalent weight of levodopa ranging from 10 mg to 10 g. "Unit dosage form" refers to a physically discrete unit suitable as a unitary dosage for humans and other mammals, each unit containing a predetermined quantity of active material calculated to produce the desired therapeutic effect, in association with a suitable pharmaceutical excipient, diluent, carrier and/or adjuvant.

A levodopa prodrug can be administered in a therapeutically effective amount. It will be understood, however, that the amount of the compound actually administered will be determined by a physician, in the light of the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient can be mixed with a pharmaceutical excipient, diluent, carrier and/or adjuvant to form a solid preformulation composition containing a homogeneous mixture containing the levodopa prodrug. When referring to these preformulation compositions as homogeneous, it is meant that the prodrug is dispersed evenly throughout the composition so that the composition can be readily subdivided into equally effective unit dosage forms such as tablets, pills and capsules. This solid preformulation can then be subdivided into unit dosage forms of the type described herein comprising, for example, a equivalent weight of levodopa ranging from 10 mg to 10 g.

Tablets or pills comprising a levodopa prodrug can be coated or otherwise compounded to provide a dosage form affording the advantage of sustained release. For example, a tablet or pill can comprise an inner dosage and an outer dosage component, the latter being in the form of an envelope over and/or enclosing the former. The two components can be separated by an enteric layer. The enteric layer can serve to resist disintegration in the stomach and permit the inner component to pass intact into the duodenum, or to delay release. A variety of materials can be used for such enteric layers or coatings. For example, such materials include a number of polymeric acids and mixtures of polymeric acids with such materials as shellac, cetyl alcohol, and cellulose acetate The liquid forms in which the compositions comprising levodopa prodrugs can be incorporated for administration orally or by injection include aqueous solutions suitably flavored syrups, aqueous or oil suspensions, and flavored emulsions with edible oils such as cottonseed oil, sesame oil, coconut oil, or peanut oil, as well as elixirs and similar pharmaceutical vehicles.

Sustained Release Oral Dosage Forms

Certain levodopa prodrugs can be practiced with a number of different dosage forms, which can be adapted to provide sustained release of the levodopa prodrug upon oral administration.

In certain embodiments, the dosage form can comprise beads that on dissolution or diffusion release the prodrug over an extended period of hours, in some embodiments, over a period of at least 4 hours, in some embodiments, over a period of at least 8 hours, over a period of at least 12 hours, over a period of at least 24 hours, and in other embodiments, over a period of more than 24 hours. The prodrug-releasing beads can have a central composition or core comprising a prodrug and pharmaceutically acceptable vehicles, including an optional lubricant, antioxidant and buffer. Suitable timed-release beads are disclosed in Lu, *Int. J. Pharm.*, 1994, 112, 117-124; Pharmaceutical Sciences by Remington, 14$^{th}$ ed, pp. 1626-1628 (1970); Fincher, *J. Pharm. Sci.*, 1968, 57, 1825-1835; and U.S. Pat. No. 4,083,949). Suitable tablets are disclosed in Pharmaceutical Sciences by Remington, 17$^{th}$ Ed, Ch. 90, pp. 1603-1625 (1985).

In certain embodiments, an oral sustained release pump can be used (see Langer, 1990, *Science*, 249:1527-1533; Sefton, 1987, CRC Crit. Ref. Biomed. Eng., 14:201; Saudek et al., 1989, *N. Engl. J. Med.,* 321:574).

In certain embodiments, polymeric materials can be used for oral sustained release delivery such as described, for example, in "Medical Applications of Controlled Release," Langer and Wise (eds.), CRC Press, Boca Raton, Fla. (1974); "Controlled Drug Bioavailability," Drug Product Design and Performance, Smolen and Ball (eds.), Wiley, New York (1984); Ranger and Peppas, 1983, *J. Macromol. Sci. Rev. Macromol Chem.,* 23:61; Levy et al., 1985, *Science,* 228: 190; During et al., 1989, *Ann. Neurol.,* 25:351; and Howard et al., 1989, *J. Neurosurg.,* 71:105.

In certain embodiments, enteric-coated preparations can be used for oral sustained release administration. In certain embodiments, coating materials include polymers with a pH-dependent solubility (i.e., pH-controlled release), polymers with a slow or pH-dependent rate of swelling, dissolution or erosion (i.e., time-controlled release), polymers that can be degraded by enzymes (i.e., enzyme-controlled release) and polymers that form firm layers that can be destroyed by an increase in pressure (i.e., pressure-controlled release).

In certain embodiments, drug-releasing lipid matrices or prodrug-releasing waxes can be used for oral sustained release administration.

In certain embodiments, a controlled-release system can be placed in proximity to the target of the levodopa prodrug, thus requiring only a fraction of the systemic dose (see Goodson, in "Medical Applications of Controlled Release," supra, vol. 2, pp. 115-138 (1984)). Other controlled-release systems discussed in Langer, 1990, *Science,* 249:1527-1533 can also be used.

In certain embodiments, a dosage form can comprise a levodopa prodrug coated on a polymer substrate. The polymer can be an erodible, or a nonerodible polymer. Representative biodegradable polymers are described, for example, in Rosoff, Controlled Release of Drugs, Chap. 2, pp. 53-95 (1989); and U.S. Pat. Nos. 3,811,444; 3,962,414; 4,066,747; 4,070,347; 4,079,038; and 4,093,709.

In certain embodiments, a dosage form can comprise a levodopa prodrug loaded into a polymer that releases the prodrug by diffusion through a polymer, or by flux through pores or by rupture of a polymer matrix as described, for example, in Coleman et al., *Polymers,* 1990, 31, 1187-1231; Roerdink et al., *Drug Carrier Systems,* 1989, 9, 57-100; Leong et al., *Adv. Drug Delivery Rev.,* 1987, 1, 199-233; Roff et al., Handbook of Common Polymers, 1971, CRC Press; and U.S. Pat. No. 3,992,518.

In certain embodiments, osmotic delivery systems can be used for oral sustained release administration (see Verma et al., *Drug Dev. Ind. Pharm.,* 2000, 26:695-708).

Regardless of the specific form of sustained release oral dosage form used, alevodopa prodrug can be released from the dosage form, e.g., an orally administered dosage form, over a sufficient period of time to provide prolonged therapeutic concentrations of levodopa in the blood of a patient enabling administration of the dosage form on only a once or twice per day basis. In certain embodiments, the levodopa prodrug can maintain a therapeutic or prophylactic blood concentration of levodopa or levodopa prodrug in the systemic circulation of a patient following oral administration of a levodopa prodrug over a period of at least 4 hours, in certain embodiments, over a period of at least 8 hours, and in certain embodiments, over a period of at least 12 hours.

The compositions can be administered for prophylactic and/or therapeutic treatments. A therapeutic amount is an amount sufficient to remedy a disease state or symptoms, or otherwise prevent, hinder, retard, or reverse the progression of disease or any other undesirable symptoms in any way whatsoever. In prophylactic applications, compositons are administered to a patient susceptible to or otherwise at risk of a particular disease or infection. Hence, a prophylactically effective amount is an amount sufficient to prevent, hinder or retard a disease state or its symptoms. The precise amount of at least one compound contained in a composition can depend on a patient's state of health and weight.

An appropriate dosage of the pharmaceutical compostion can be determined according to any one of several well-established protocols. For example, animal studies, such as studies using mice or rats, can be used to determine an appropriate dose of a pharmaceutical compound. The results from animal studies can be extrapolated to determine doses for use in other species, such as for example, humans.

In certain embodiments, the dosage forms can be administered twice per day, in some embodiments once per day, and in some embodiments, at longer intervals.

Certain embodiments can be further defined by reference to the following examples, which describe in detail preparation of compounds and compositions comprising at least one levodopa prodrug and assays for using compounds and compositions comprising at least one levodopa prodrug. It will be apparent to those skilled in the art that many modifications, both to materials and methods, can be practiced without departing from the embodiments.

EXAMPLES

The following synthetic and biological examples are offered to illustrate certain embodiments and are not to be construed in any way as limiting the scope. Unless otherwise stated, all temperatures are in degrees Celsius. In the examples below, the following abbreviations have the following meanings. If an abbreviation is not defined, it has its generally accepted meaning.

Boc=tert-butyloxycarbonyl
DCC=dicyclohexylcarbodiimide
DCM=dichloromethane
DMAP=4-N,N-dimethylaminopyridine
EDTA=ethylenediaminetetraacetic acid
g=gram
hr=hour
HPLC=high pressure liquid chromatography
L=liter
LC/MS=liquid chromatography/mass spectroscopy
M=molar
mg=milligram
min=minute
mL=milliliter
mmol=millimoles
Pd—C=palladium on activate carbon
THF=tetrahydrofuran
μg=microgram
μL=microliter
μM=micromolar Example 1

1(R)- and 1(S)-Cyclohexyloxycarbonylethyl

2(S)-amino-3-(3,4-dihydroxyphenyl)-propanoate

To a mixture of cyclohexanol (10.9 g, 10.9 mmol), pyridine (8.62 g, 10.9 mmol) in dichloromethane was added 2-bromopropionyl chloride (18.53 g, 10.9 mmol) at 0° C. The resulting mixture was stirred at room temperature for 1 hr. The product was partitioned between hexane and 10% citric acid. The organic phase was separated, dried over $MgSO_4$ and concentrated to yield 2-bromo-propionic acid cyclohexyl ester, which was used in the following reaction without further purification.

To a suspension of compound Boc-DOPA (297 mg, 1 mmol) and cesium hydrogencarbonate (194 mg, 1 mmol) in acetone was added 2-bromo-propionic acid cyclohexyl ester (235 mg, 1 mmol) and the resulting mixture was stirred at 55° C. for 40 hrs. After removing the solvent, the residue was partitioned between ethyl acetate and 10% citric acid. The organic phase was separated, dried over $MgSO_4$, and concentrated. The resulting residue was then treated with 30% trifluoroacetic acid in dichloromethane at room temperature for 30 min. After removing the solvent, the resulting residue was purified by reverse phase preparative HPLC to afford 40 mg of a mixture of two diastereoisomers of the title compounds. MS (ESI) m/z 352.73 $(M+H)^+$.

Example 2

1(R)- and 1(S)-Isoproxycarbonylethyl 2(S)-amino-3-(3,4-dihydroxy-phenyl)-propanoate Following the procedure described in Example 1, and substituting cyclohexanol with isopropanol, provided a mixture of two diastereoisomers of the title compound. MS (ESI) m/z 312.70 $(M+H^+)^+$.

Example 3

2-Phenylcarbonyloxyethyl (2S)-2-amino-3-(3,4-dihydroxyphenyl)propanoate hydrochloride Step A: Bromoethyl Benzoate To a solution of benzoic acid (2.44 g, 20 mmol) and 2-bromoethan-1-ol (1.42 mL, 20 mmol) in 40 mL of anhydrous dichloromethane, a solution of 1,3-dicyclohexylcarbodiimide (4.12 g, 20 mmol) in dichloromethane was slowly added followed by addition of a catalytic amount of 4-(dimethylamino)pyridine. The resulting mixture was stirred at room temperature for 16 hrs. After filtration, the filtrate was washed with 5% $NaHCO_3$, brine, and dried over $Na_2SO_4$. After removing the solvent, chromatography (silica gel, 10% ethyl acetate in hexane) of the residue gave 3.7 g (82%) of the title compound. $^1H$ NMR (400 MHz, $CDCl_3$): δ 3.62 (t, J=6 Hz, 2H), 4.60 (t, J=6 Hz, 2H), 7.42 (m, 2H), 7.54 (m, 2H), 8.04 (m, 2H).

Step B: 2-Phenylcarbonyloxyethyl (2S)-2-amino-3-(3,4-dihydroxyphenyl)propanoate hydrochloride A suspension of bromoethyl benzoate (2.29 g, 10 mmol), N-Boc-L-DOPACOOH (3.2 g, 11 mmol), and cesium bicarbonate (2.1 g, 11 mmol) in N,N-dimethylacetamide (50 mL) was stirred at 55° C. for 16 hrs. The solvent was evaporated under vacuum. The resulting residue was dissolved in ethyl acetate, washed with water, 5% $NaHCO_3$, brine, and dried over $Na_2SO_4$. After removing the solvent, chromatography (silica gel, 30% ethyl acetate in hexane) of the residue gave 3.8 g of a white solid. The white solid was treated with 4M HCl in dioxane at room temperature for 30 min. After removing the solvent, the resulting solid was dissolved in 10 mL of anhydrous acetonitrile and refrigerated. The resulting white precipitate was filtered, washed with ether, and dried under vacuum to afford 2.2 g (58%) of the title compound.

$^1$H NMR (400 MHz, $CD_3OD$): δ 3.02 (dd, J=7.2, 14.4 Hz, 1H), 3.11 (dd, J=5.6, 14.4 Hz, 1H), 4.25 (t, J=6.4 Hz, 1H), 4.52-4.64 (m, 4H), 6.53 (dd, J=2, 8 Hz, 1H), 6.67 (d, J=2 Hz, 1H), 6.69 (d, J=8 Hz, 1H), 7.47 (t, J=7.6 Hz, 2H), 7.60 (t, J=7.6 Hz, 1H), 8.02 (d, J=7.6 Hz, 2H). MS (ESI) m/z 346.17 $(M+H)^+$ and 344.13 $(M-H)^-$.

Example 4

2-(4-Fluorophenylcarbonyloxy)ethyl (2S)-2-amino-3-(3,4-dihydroxyphenyl)propanoate hydrochloride Following the procedure described in Example 3 and substituting benzoic acid with 4-fluorobenzoic acid, provided the title compound (62% over 2 steps) as a white solid. $^1$H NMR (400 MHz, $CD_3OD$): δ 3.03 (dd, J=6.8, 14.4 Hz, 1H), 3.11 (dd, J=6, 14.4 Hz, 1H), 4.26 (t, J=6.4 Hz, 1H), 4.50-4.63 (m, 4H), 6.53 (dd, J=2, 8 Hz, 1H), 6.67 (d, J=2 Hz, 1H), 6.69 (d, J=8 Hz, 1H), 7.20 (t, J=8.8 Hz, 2H), 8.05 (dd, J=5.2, 8.8 Hz, 2H). MS (ESI) m/z 363.92 $(M+H)^+$ and 362.02 $(M-H)^-$.

Example 5

3-Phenylcarbonyloxypropyl (2S)-2-amino-3-(3,4-dihydroxyphenyl)propanoate hydrochloride Following the procedure described in Example 3 and substituting 2-bromoethan-1-ol with 3-bromopropan-1-ol provided the title compound (61% over 2 steps) as a white solid. $^1$H NMR (400 MHz, $CD_3OD$): δ 2.40 (m, 2H), 3.02 (dd, J=7.2, 14.4 Hz, 1H), 3.09 (dd, J=6.4, 14.4 Hz, 1H), 4.20 (t, J=6.4 Hz, 1H), 4.35 (t, J=6.4 Hz, 1H), 4.37 (t, J=6.4 Hz, 1H), 6.53 (dd, J=2, 8 Hz, 1H), 6.66 (d, J=2 Hz, 1H), 6.73 (d, J=8 Hz, 1H), 7.48 (t, J=8 Hz, 2H), 7.61 (t, J=8.0 Hz, 1H), 8.01 (m, 2H). MS (ESI) m/z 360.13 $(M+H)^+$ and 358.06 $(M-H)^-$.

Example 6

3-(4-Fluorophenylcarbonyloxy)propyl (2S)-2-amino-3-(3,4-dihydroxyphenyl)propanoate hydrochloride Following the procedure described in Example 3 substituting benzoic acid with 4-fluorobenzoic acid and 2-bromoethan-1-ol with 3-bromopropan-1-ol respectively, provided the title compound (55% over 2 steps) as a white solid. $^1$H NMR (400 MHz, $CD_3OD$): δ 2.12 (m, 2H), 3.03 (dd, J=7.2, 14.4 Hz, 1H), 3.09 (dd, J=6.4, 14.4 Hz, 1H), 4.21 (t, J=7.2 Hz, 1H), 4.35 (t, J=6.4 Hz, 1H), 4.37 (t, J=6.4 Hz, 1H), 6.54 (dd, J=2, 8 Hz, 1H), 6.67 (d, J=2 Hz, 1H), 6.73 (d, J=8 Hz, 1H), 7.21 (t, J=8.8 Hz, 2H), 8.07 (dd, J=5.6, 8.8 Hz, 2H). MS (ESI) m/z 378.27 $(M+H)^+$ and 376.24 $(M-H)^-$.

Example 7

2-Acetyloxyethyl (2S)-2-amino-3-(3,4-dihydroxyphenyl)propanoate hydrochloride Following the procedure step 2 described in Example 3 and substituting of 2-bromoethyl with 2-bromoethyl acetate, provided the title compound, which was purified by using HPLC (0.05% formic acid/water/acetonitrile) followed by lyophilization in the presence of hydrochloride. $^1$H NMR (400 MHz, $CD_3OD$): δ 2.50 (s, 3H), 3.03 (dd, J=6.8, 14.4 Hz, 1H), 3.11 (dd, J=6.4, 14.4 Hz, 1H), 4.24 (t, J=6.4 Hz, 1H), 4.27 (t, J=7.2 Hz, 2H), 4.44 (m, 2H), 6.55 (dd, J=2, 8 Hz, 1H), 6.67 (d, J=2 Hz, 1H), 6.73 (d, J=8 Hz, 1H). MS (ESI) m/z 284.10 $(M+H)^+$ and 282.13 $(M-H)^-$.

Example 8

(2R)-2-Phenylcarbonyloxypropyl (2S)-2-amino-3-(3,4-dihydroxyphenyl)propanoate hydrochloride Step A: (2R)-1-(tert-Butyldimethyl-1-silyloxy)propan-2-ol (R)-(−)-1,2-propanediol (5 g, 65.7 mmol) and imidazole (4.47 g, 65.7 mmol) was dissolved in anhydrous dichloromethane (40 mL). A solution of tert-butyldimethylchlorosilane (9.9 g, 65.7 mmol) in dichloromethane was added at 0° C. The mixture was stirred at 0° C. for 2 hrs. After filtration the filtrate was dried over $Na_2SO_4$ and concentrated to afford 12.5 g (100%) of the title compound, which was used in the next reaction step without further purification. $^1$H NMR (400 MHz, $CDCl_3$): δ 0 (s, 6H), 0.83 (s, 9H), 1.04 (d, J=6.4 Hz, 3H), 2.64 (s, br, 1H), 3.26 (dd, J=8, 9.6 Hz, 1H), 3.50 (dd, J=3.2, 9.6 Hz, 1H), 3.74 (m, 1H).

Step B: (1R)-1-Methyl-2-(tert-butyldimethylsilyloxy)ethyl benzoate

Benzoic acid (2.44 g, 20 mmol) and (2R)-1-(tert-butyldimethyl-1-silyloxy)propan-2-ol (4.18 g, 22 mmol) was dissolved in 40 mL of anhydrous dichloromethane. A solution of 1,3-dicyclohexylcarbodiimide (4.94 g, 24 mmol) in dichloromethane was added slowly, followed by a catalytic amount of 4-(dimethylamino)pyridine. The mixture was stirred at room temperature for 16 hrs. After filtration, the filtrate was washed with 5% $NaHCO_3$, brine, and dried over $Na_2SO_4$. After removing the solvent, chromatography (silica gel, 10% ethyl acetate in hexane) of the residue provided 5.8 g (98%) of the title compound. $^1$H NMR (400 MHz, $CDCl_3$): δ 0 (s, 3H), 0.2 (s, 3H), 0.83 (s, 9H), 1.30 (d, J=6.4 Hz, 1H), 3.66 (dd, J=4.8, 10.8 Hz, 1H), 3.72 (dd, J=5.6, 10.8 Hz, 1H), 5.15 (m, 1H), 7.36 (t, J=8.4 Hz, 2H), 7.48 (t, J=8.4 Hz, 1H), 7.98 (d, J=8.4 Hz, 2H).

Step C: (1R)-2-Hydroxy-isopropyl benzoate (1R)-1-methyl-2-(tert-butyldimethylsilyloxy)ethyl benzoate (5.8 g, 19.7 mmol) was dissolved in anhydrous tetrahydrofuran. Triethylamine trihydrofluoride was added slowly. The mixture was stirred at room temperature for 8 hrs, and the solvent was evaporated under reduced pressure. Chromatography (silica gel, 30% ethyl acetate in hexane) of the residue provided 3.2 g (90%) of the title compound. $^1$H NMR (400 MHz, $CDCl_3$): δ 1.37 (d, J=6.4 Hz, 1H), 2.30 (t, J=6.4 Hz, 1H), 3.78 (m, 1H), 5.23 (m, 1H), 7.42 (t, J=7.6 Hz, 2H), 7.54 (t, J=7.6 Hz, 1H), 8.03 (d, J=7.6 Hz, 2H).

Step D: (1R)-2-Bromo-isopropyl benzoate

To a suspension of dibromotriphenylphosphorane (9 g, 21.3 mmol) in anhydrous dichloromethane, a solution of (1R)-2-hydroxyisopropyl benzoate (3.2 g, 17.7 mmol) in dichloromethane was added slowly at 0° C. The mixture was stirred at 0° C. to room temperature for 16 hrs, then washed with water, 5% NaHCO$_3$, brine, and dried over Na$_2$SO$_4$. After concentration, hexane was added to the resulting residue. Ph$_3$PO was precipitated. After filtration and thoroughly washing with hexane, the filtrate was concentrated. Chromatography of the residue with silica gel eluting with 10% ethyl acetate in hexane afforded 3.6 g (85%) of the title compound. $^1$H NMR (400 MHz, CDCl$_3$): δ 1.47 (d, J=6.4 Hz, 3H), 3.75 (m, 2H), 5.31 (m, 1H), 7.42 (t, J=8 Hz, 2H), 7.54 (t, J=8 Hz, 1H), 8.04 (d, J=8 Hz, 2H).

Step F: (2R)-2-Phenylcarbonyloxypropyl (2S)-2-amino-3-(3,4-dihydroxyphenyl)propanoate hydrochloride A suspension of (1R)-2-bromoisopropyl benzoate (4.98 g, 20.6 mmol), N-Boc-L-DOPA-COOH (7.3 g, 25 mmol), and cesium bicarbonate (4.85 g, 25 mmol) in N,N-dimethylacetamide (100 mL) was stirred at 55° C. for 16 hrs. The solvent was evaporated under vacuum. To the residue was added ethyl acetate and the resulting solution was washed with water, 5% NaHCO$_3$, brine, and dried over Na$_2$SO$_4$. After removing the solvent under reduced pressure, chromatography (silica gel, 30% ethyl acetate in hexane) of the residue gave 6.3 g (68%) of a white solid. The white solid was treated with 50 mL of 4M HCl in dioxane at room temperature for 30 min. The reaction mixture was concentrated to dryness under reduced pressure. The resulting residue was dissolved in about 20 mL of anhydrous acetonitrile and 4 mL of ether. The solution was refrigerated, and the resulting white precipitate was filtered, washed with ether, and dried under vacuum to afford 4.7 g (87%) of the title compound. $^1$H NMR (400 MHz, CD$_3$OD): δ 1.40 (d, J=6.4 Hz, 3H), 2.99 (dd, J=7.6, 14.4 Hz, 1H), 3.10 (dd, J=5.6, 14.4 Hz, 1H), 4.24 (dd, J=6, 8 Hz, 1H), 4.38 (dd, J=6.8, 11.6 Hz, 1H), 4.52 (dd, J=3.2, 11.6 Hz, 1H), 5.40 (m, 1H), (1H, dd, J=2, 8 Hz, 1H), 6.66 (d, J=2 Hz, 1H), 6.69 (d, J=8 Hz, 1H), 7.47 (t, J=7.6 Hz, 2H), 7.60 (t, J=7.6 Hz, 1H), 8.02 (d, J=7.6 Hz, 2H). MS (ESI) m/z 360.15 (M+H)$^+$ and 358.09 (M−H)$^-$.

Example 9

(2S)-2-Phenylcarbonyloxypropyl (2S)-2-amino-3-(3,4-dihydroxyphenyl)propanoate hydrochloride Following the procedure described in Example 8, and substituting (R)-(−)-1,2-dipropanediol with (S)-(+)-1,2-dipropanediol, provided the title compound (32% over 5 steps) as a white solid. $^1$H NMR (400 MHz, CD$_3$OD): δ 1.37 (d, J=6.4 Hz, 3H), 2.94 (dd, J=7.2, 14.4 Hz, 1H), 3.05 (dd, J=6, 14.4 Hz, 1H), 4.23 (t, J=6.4 Hz, 1H), 4.40 (dd, J=5.2, 11.6 Hz, 1H), 4.47 (dd, J=3.6, 11.6 Hz, 1H), 5.40 (m, 1H), 6.48 (dd, J=2, 8 Hz, 1H), 6.64 (d, J=2 Hz, 1H), 6.69 (d, J=8 Hz, 1H), 7.47 (t, J=8 Hz, 2H), 7.60 (t, J=7.2 Hz, 1H), 8.00 (d, J=8 Hz, 2H). MS (ESI) m/z 360.33 (M+H)$^+$ and 358.31 (M−H)$^-$.

Example 10

(2R)-2-(4-Fluorophenylcarbonyloxy)propyl (2S)-2-amino-3-(3,4-dihydroxyphenyl)propanoate hydrochloride Following the procedure described in Example 8 and substituting benzoic acid with 4-fluorobenzoic acid, provided the title compound (23% over 5 steps) as a white solid. $^1$H NMR (400 MHz, CD$_3$OD): δ 1.38 (d, J=6.4 Hz, 3H), 3.01 (dd, J=7.2, 14.4 Hz, 1H), 3.09 (dd, J=5.6, 14.4 Hz, 1H), 4.23 (t, J=6.4 Hz, 1H), 4.37 (dd, J=6.4, 11.6 Hz, 1H), 4.49 (dd, J=3.2, 11.6 Hz, 1H), 5.36 (m, 1H), 6.53 (dd, J=2, 8 Hz, 1H), 6.67 (d, J=2 Hz, 1H), 6.69 (d, J=8 Hz, 1H), 7.20 (t, J=8.8 Hz, 2H), 8.05 (dd, J=5.6, 8.8 Hz, 2H). MS (ESI) m/z 378.11 (M+H)$^+$ and 376.06 (M−H)$^-$.

Example 11

(2S)-2-(4-Fluorophenylcarbonyloxy)propyl (2S)-2-amino-3-(3,4-dihydroxyphenyl)propanoate hydrochloride Following the procedure described in Example 8 substituting benzoic acid with 4-fluorobenzoic acid and (R)-(−)-1,2-propanediol with (S)-(+)-1,2-propanediol separately, provided the title compound (43% over 5 steps) as a white solid. $^1$H NMR (400 MHz, CD$_3$OD): δ 1.36 (d, J=6.4 Hz, 3H), 2.96 (dd, J=7.2, 14.4 Hz, 1H), 3.05 (dd, J=6, 14.4H, 1 Hz), 4.24 (dd, J=6, 6.8 Hz, 1H), 4.38 (dd, J=6.8, 11.6 Hz, 1H), 4.46 (dd, J=3.2, 11.6 Hz, 1H), 5.38 (m, 1H), 6.49 (dd, J=2, 8 Hz, 1H), 6.64 (d, J=2 Hz, 1H), 6.71 (d, J=8 Hz, 1H), 7.20 (t, J=8.8 Hz, 2H), 8.05 (dd, J=5.6, 8.8 Hz, 2H). MS (ESI) m/z 378.48 (M+H)$^+$ and 376.34 (M−H)$^-$.

Example 12

(1R)-1-Methyl-2-phenylcarbonyloxyethyl (2S)-2-amino-3-(3,4-dihydroxyphenyl)propanoate hydrochloride Step A: (2R)-1-(tert-Butyldimethyl-1-silyloxy)propan-2-ol (R)-(−)-1,2-propanediol (5 g, 65.7 mmol) and imidazole (4.47 g, 65.7 mmol) was dissolved in anhydrous dichloromethane. A solution of chlorodimethylt-butylsilane (9.9 g, 65.7 mmol) in dichloromethane was added at 0° C. The mixture was stirred at 0° C. for 2 hrs. After filtration the filtrate was dried over Na$_2$SO$_4$. Concentration gave 12.5 g (100%) of (2R)-1-(tert-Butyldimethyl-1-silyloxy)propan-2-ol, which was used in the next reaction without further purification. $^1$H NMR (400 MHz, CDCl$_3$): δ 0 (s, 6H), 0.83 (s, 9H), 1.04 (d, J=6.4 Hz, 3H), 2.64 (s, br, 1H), 3.26 (dd, J=8, 9.6 Hz, 1H), 3.50 (dd, J=3.2, 9.6 Hz, 1H), 3.74 (m, 1H).

Step B: (1R)-1-Methyl-2-(tert-butyldimethylsilyloxy)ethyl (2S)-2-[(tert-butoxy)carbonylamino]-3-[3,4-bis(phenylmethoxy)phenyl]propanoate N-Boc-L-DOPA(OBn)$_2$—COOH (3.6 g, 7.5 mmol) was dissolved in anhydrous dichloromethane. Triethylamine (2.6 mL, 18.5 mmol), and 2,4,6-trichlorobenzoyl chloride (1.4 mL, 9 mmol) were added and the solution stirred for 30 min. A solution of (2R)-1-(tert-butyldimethyl-1-silyloxy)propan-2-ol (1.7 g, 9 mmol) in dichloromethane was slowly added to the reaction mixture, followed by the addition of a catalytic amount of 4-(dimethylamino)pyridine. The resulting mixture was stirred at room temperature for 16 hrs, then washed with 10% citric acid, dried over $Na_2SO_4$, and concentrated. Chromatography (silica gel, 10% ethyl acetate in hexane) afforded 3.4 g (70%) of (1R)-1-Methyl-2-(tert-butyldimethylsilyloxy)ethyl (2S)-2-[(tert-butoxy)carbonylamino]-3-[3,4-bis(phenylmethoxy)phenyl]propanoate. $^1$H NMR (400 MHz, $CDCl_3$): δ 0.08 (s, 6H), 0.88 (s, 9H), 1.12 (d, J=6.4 Hz, 3H), 1.42 (s, 9H), 2.99 (m, 2H), 3.35 (m, 1H), 3.59 (m, 1H), 3.84 (m, 1H), 4.50 (m, 1H), 4.89 (d, NH, 1H), 5.10 (s, 4H), 6.60 (d, J=8 Hz, 1H), 6.71 (s, 1H), 6.87 (d, J=8 Hz, 1H), 7.26-7.43 (m, 10H).

Step C: (1R)-2-Hydroxy-isopropyl (2S)-2-[(tert-butoxy)carbonylamino]-3-[3,4-bis(phenylmethoxy)phenyl]propanoate (1R)-1-Methyl-2-(tert-butyldimethylsilyloxy)ethyl (2S)-2-[(tert-butoxy)carbonylamino]-3-[3,4-bis(phenylmethoxy)phenyl]propanoate (3.4 g, 5.2 mmol) was dissolved in anhydrous tetrahydrofuran. Triethylamine trihydrofluoride was added slowly. The mixture was stirred at room temperature for 4 hours, and the solvent was evaporated under reduced pressure. Chromatography (silica gel, 30% ethyl acetate in hexane) provided 2.5 g (90%) of (1R)-2-Hydroxy-isopropyl (2S)-2-[(tert-butoxy)carbonylamino]-3-[3,4-bis(phenylmethoxy)phenyl]propanoate. $^1$H NMR (400 MHz, $CDCl_3$): δ 1.09 (d, J=6.4 Hz, 3H), 1.41 (s, 9H), 2.78 (s, br, 1H), 2.96 (m, 2H), 3.51 (m, 1H), 3.59 (m, 1H), 4.34 (m, 1H), 4.98 (m, 1H), 5.05 (d, NH, 1H), 5.10 (s, 4H), 6.66 (d, J=8 Hz, 1H), 6.77 (s, 1H), 6.83 (d, J=8 Hz, 1H), 7.26-7.43 (m, 10H).

Step D: (1R)-1-Methyl-2-phenylcarbonyloxyethyl (2S)-2-[(tert-butoxy)carbonylamino]-3-[3,4-bis(phenylmethoxy)phenyl]propanoate To a solution of benzoic acid (0.57 g, 4.67 mmol) and (1R)-2-hydroxy-isopropyl (2S)-2-[(tert-butoxy)carbonylamino]-3-[3,4-bis(phenylmethoxy)phenyl]propanoate (2.5 g, 4.67 mmol) was dissolved in 60 mL of anhydrous dichloromethane was slowly added a solution of 1,3-dicyclohexylcarbodiimide (1.15 g, 5.6 mmol) in dichloromethane followed by a catalytic amount of 4-(dimethylamino)pyridine. The resulting mixture was stirred at room temperature for 16 hrs. After filtration, the filtrate was washed with 5% $NaHCO_3$ and dried over $Na_2SO_4$. After removing the solvent, chromatography (silica gel, 10% ethyl acetate in hexane) of the residue provided 2.6 g (87%) of (1R)-1-Methyl-2-phenylcarbonyloxyethyl (2S)-2-[(tert-butoxy)carbonylamino]-3-[3,4-bis(phenylmethoxy)phenyl]propanoate. $^1$H NMR (400 MHz, $CDCl_3$): δ 1.23 (d, J=6.4 Hz, 3H), 1.41 (s, 9H), 2.98 (m, 2H), 4.26 (m, 1H), 4.33 (m, 1H), 4.51 (m, 1H), 4.93 (d, NH, 1H), 5.10 (s, 4H), 5.24 (m, 1H), 6.65 (d, J=8 Hz, 1H), 6.76 (s, 1H), 6.81 (d, J=8 Hz, 1H), 7.25-7.45 (m, 12H), 7.54 (t, J=7.6 Hz, 1H), 8.00 (d, J=7.6 Hz, 2H).

Step E: (1R)-1-Methyl-2-phenylcarbonyloxyethyl (2S)-3-(3,4-dihydroxyphenyl)-2-[(tert-butoxy)carbonylamino]propanoate To a solution of (1R)-1-methyl-2-phenylcarbonyloxyethyl (2S)-2-[(tert-butoxy)carbonylamino]-3-[3,4-bis(phenylmethoxy)phenyl]propanoate (2.6 g, 4.85 mmol) in 40 mL of tetrahydrafuran was added 200 mg of 10% Pd—C pre-mixed with 10 mL of methanol under a nitrogen atmosphere. The resulting mixture was stirred under hydrogen at room temperature for 2 hrs. After filtration and washing with methanol, the filtrate was concentrated and chromatography of the residue (silica gel, 30% ethyl acetate in hexane) afforded 1.87 g (100%) of (1R)-1-Methyl-2-phenylcarbonyloxyethyl (2S)-3-(3,4-dihydroxyphenyl)-2-[(tert-butoxy)carbonylamino]propanoate. MS (ESI) m/z 460.20 $(M+H)^+$ and 458.17 $(M-H)^-$.

Step F: (1R)-1-Methyl-2-phenylcarbonyloxyethyl (2S)-2-amino-3-(3,4-dihydroxyphenyl)propanoate hydrochloride (1R)-1-Methyl-2-phenylcarbonyloxyethyl (2S)-3-(3,4-dihydroxyphenyl)-2-[(tert-butoxy)carbonylamino]propanoate (1.87 g, 4 mmol) was dissolved in 40 mL of 4M HCl in dioxane. The resulting mixture was stirred at room temperature for 30 min. Dioxane was evaporated completely under reduced pressure. The resulting white solid was dissolved in acetonitrile (5 mL), and ether added until the solution became slightly cloudy. The solution was refrigerated overnight and the product was crystallized. The white crystalline solid was collected and dried under vacuum to afford 1.5 g (93%) of the title compound. $^1$H NMR (400 MHz, $CD_3OD$): δ 1.35 (d, J=6.4 Hz, 3H), 3.01 (dd, J=6.8, 14.4 Hz, 1H), 3.08 (dd, J=6.4, 14.4 Hz, 1H), 4.19 (t, J=6.4 Hz, 1H), 4.34 (dd, J=6, 12.4 Hz, 1H), 4.49 (dd, J=2.8, 12.4 Hz, 1H), 5.35 (m, 1H), 6.55 (dd, J=2, 8 Hz, 1H), 6.66 (d, J=2 Hz, 1H), 6.71 (d, J=8 Hz, 1H), 7.48 (t, J=7.2 Hz, 2H), 7.61 (t, J=7.2 Hz, 1H), 8.02 (d, J=7.6 Hz, 2H). MS (ESI) m/z 360.16 $(M+H)^+$ and 358.13 $(M-H)^-$.

Alternatively, (1R)-1-Methyl-2-phenylcarbonyloxyethyl (2S)-2-[(tert-butoxy)carbonylamino]-3-[3,4-bis(phenylmethoxy)phenyl]propanoate (Step D in Example 12) can be prepared as follows:

Step A (Epoxide Opening Method): (2R)-2-Hydroxypropyl benzoate

A solution of (R)-(+)-propylene oxide (10.5 mL, 150 mmol), benzoic acid (12.2 g, 100 mmol), and tetrabutylammonium bromide (3.22 g, 10 mmol) in anhydrous acetonitrile was heated to 50° C. in a sealed pressure vessel for 24 hrs. The reaction mixture was concentrated to dryness under reduced pressure, diluted with ethyl acetate, and washed with water twice followed by the addition of saturated $NaHCO_3$ solution and brine. The organic layer was dried through $MgSO_4$ and concentrated under reduced pressure to afford 18.0 g (100%) of a mixture of (2R)-2-Hydroxypropyl benzoate and its regio-isomer (1R)-2-Hydroxy-isopropyl benzoate with a ratio of 7.2:1. A solution of the mixture of regio-isomers (1.8 g, 10 mmol) and 2,4,6-collidine (1.1 mL, 8 mmol) in 50 mL of anhydrous dichloromethane was cooled to −78° C. before acetyl chloride (0.28 mL, 4 mmol) was added dropwise. The reaction mixture was stirred at −78° C. for 3 hrs before being warmed to room temperature over 1 h. The reaction mixture was diluted with dichloromethane and washed three times with 0.5N HCl followed by the addition of brine. The organic layer was dried through $MgSO_4$ and concentrated under reduced pressure. Chromatography (silica gel, 1:2.5 ethyl acetate/hexane) afforded 1.6 g (89%) of (2R)-2-Hydroxypropyl benzoate.

Step A (Diol Benzoylation Method): (2R)-2-Hydroxypropyl benzoate

Benzoyl chloride (10.98 mL, 94.62 mmol) was added dropwise to a solution of (R)-(−)-1,2-propanediol (6.00 g, 78.85 mmol) and 2,4,6-collidine (7.22 mL, 54.67 mmol) in 100 mL of anhydrous dichloromethane at −78° C. The reaction was stirred at −78° C. for three hours and at room temperature for 1 hr, before quenching with water (10 mL) for 15 minutes. The quenched mixture was washed with 0.5N HCl (4×50 mL) until the dark color diminished, and then with saturated NaHCO$_3$ solution (4×50 mL) and brine. The organic layer was separated, dried over Na$_2$SO$_4$ and concentrated. Chromatography (silica gel 230-400 Mesh, 1:9 ethyl acetate/Hexane) of the residue afforded 8.9 g (63%) of (2R)-2-Hydroxypropyl benzoate as a white solid. $^1$H NMR (400 MHz, DMSO-d$_6$): δ 1.13 (d, J=6.4 Hz, 3H), 3.93 (m, 1H), 4.10 (m, 2H), 4.95 (d, J=4.8 Hz, 1H), 7.51 (t, J=7.2 Hz, 2H), 7.64 (t, J=7.6 Hz, 1H), 7.99 (d, J=6.8 Hz, 2H); MS (ESI) m/z 181 (M+H)$^+$.

Step B: (1R)-1-Methyl-2-phenylcarbonyloxyethyl (2S)-2-[(tert-butoxy)carbonylamino]-3-[3,4-bis(phenylmethoxy)phenyl]propanoate To a solution of (2S)-2-[(tert-butoxy)carbonylamino]-3-[3,4-bis(phenylmethoxy)phenyl]propanoic acid (15.9 g, 33.3 mmol), (2R)-2-hydroxypropyl benzoate (5.0 g, 27.7 mmol), and 4-(dimethylamino)pyridine (340 mg) in 250 mL of anhydrous dichloromethane, 1-(3-dimethylaminopropyl) 3-ethylcarbodiimide hydrochloride (EDAC) (8.0 g, 41.6 mmol) was slowly added. The resulting mixture was stirred at room temperature for 16 hrs. The reaction mixture was diluted with dichloromethane and washed with 0.5N HCl twice, followed by the addition of brine. The organic layer was separated, dried through a MgSO$_4$ pad and concentrated under reduced pressure. Chromatography (silica gel, 1:5 then 1:4 ethyl acetate/hexane) of the residue followed by crystallization from 1:5 ethyl acetate/hexane afforded 8.0 g (45%) of the title compound.

Example 13

(1S)-1-Methyl-2-phenylcarbonyloxyethyl (2S)-2-amino-3-(3,4-dihydroxyphenyl)propanoate hydrochloride Following the procedure described in Example 12 and substituting (R)-(−)-1,2-propanediol with (S)-(+)-1,2-propanediol, provided the title compound (41% over 6 steps) as a white solid. $^1$H NMR (400 MHz, CD$_3$OD): δ 1.41 (d, J=6.4 Hz, 3H), 2.92 (dd, J=8, 14.8 Hz, 1H), 3.10 (dd, J=5.2, 14.8 Hz, 1H), 4.23 (t, J=6.4 Hz, 1H), 4.38 (dd, J=7.2, 12.4 Hz, 1H), 4.47 (dd, J=3.2, 12.4 Hz, 1H), 5.42 (m, 1H), 6.51 (dd, J=2, 8 Hz, 1H), 6.65 (d, J=2 Hz, 1H), 6.67 (d, J=8 Hz, 1H), 7.47 (t, J=8.8 Hz, 2H), 7.60 (t, J=8.8 Hz, 2H), 8.02 (m, 2H). MS (ESI) m/z 360.21 (M+H)$^+$ and 358.13 (M−H)$^−$.

Example 14

(1R)-1-Methyl-2-(4-fluorophenylcarbonyloxy)ethyl (2S)-2-amino-3-(3,4-dihydroxyphenyl)propanoate hydrochloride Following the procedure described in Example 12 and substituting benzoic acid with 4-fluorobenzoic acid, provided the title compound (33% over 6 steps) as a white solid. $^1$H NMR (400 MHz, CD$_3$OD): δ 1.34 (d, J=6.4 Hz, 3H), 3.04 (dd, J=6.8, 14.4 Hz, 1H), 3.08 (dd, J=5.6, 14.4 Hz, 1H), 4.20 (t, J=6.4 Hz, 1H), 4.32 (dd, J=6, 11.6 Hz, 1H), 4.48 (dd, J=3.2, 11.6 Hz, 1H), 5.36 (m, 1H), 6.55 (dd, J=2, 8 Hz, 1H), 6.68 (d, J=2 Hz, 1H), 6.74 (d, J=8 Hz, 1H), 7.22 (t, J=8.8 Hz, 2H), 8.05 (dd, J=5.6, 8.8 Hz, 2H). MS (ESI) m/z 378.11 (M+H)$^+$ and 376.03 (M−H)$^−$.

Example 15

(1S)-1-Methyl-2-(4-fluorophenylcarbonyloxy)ethyl (2S)-2-amino-3-(3,4-dihydroxyphenyl)propanoate hydrochloride Following the procedure described in Example 12, substituting benzoic acid with 4-fluorobenzoic acid and (R)-(−)-1,2-propanediol with (S)-(+)-1,2-propanediol, provided the title compound (46% over 6 steps) as a white solid. $^1$H NMR (400 MHz, CD$_3$OD): δ 1.41 (d, J=6.4 Hz, 3H), 2.94 (dd, J=7.6, 14.4 Hz, 1H), 3.08 (dd, J=6, 14.4 Hz, 1H), 4.20 (t, J=7.2 Hz, 1H), 4.36 (dd, J=6.8, 11.2 Hz, 1H), 4.46 (dd, J=2.8, 11.2 Hz, 1H), 5.41 (m, 1H), 6.51 (dd, J=2, 8 Hz, 1H), 6.66 (d, J=2 Hz, 1H), 6.72 (d, J=8 Hz, 1H), 7.20 (t, J=8.8 Hz, 2H), 8.04 (dd, J=5.6, 8.8 Hz, 2H). MS (ESI) m/z 378.16 (M+H)$^+$ and 376.10 (M−H)$^−$.

Example 16

(1R,2R)-1-Methyl-2-phenylcarbonyloxypropyl (2S)-2-amino-3-(3,4-dihydroxyphenyl)propanoate hydrochloride

Step A: (1R,2R)-2-Hydroxy-1-methylpropyl (2S)-2-[(tert-butoxy)carbonylamino]-3-[3,4-bis(phenylmethoxy)phenyl]propanoate N-Boc-L-DOPA(OBn)$_2$COOH (4.3 g, 9 mmol) was dissolved in anhydrous dichloromethane. Triethylamine (3 mL, 22 mmol), and 2,4,6-trichlorobenzoyl chloride (1.7 mL, 11 mmol) were added and the solution stirred for 30 min. A solution of (2R,3R-(−)-2,3-butanediol (1.0 mL, 11 mmol) in dichloromethane was slowly added to the reaction mixture followed by the addition of a catalytic amount of 4-(dimethylamino)pyridine. The resulting mixture was stirred at room temperature for 16 hours, then washed with 10% citric acid, 5% NaHCO$_3$, brine, and dried over Na$_2$SO$_4$. After removing the solvent, chromatography (silica gel, gradient of 20%-30% ethyl acetate in hexane) of the residue afforded 3.4 g (69%) of (1R,2R)-2-Hydroxy-1-methylpropyl (2S)-2-[(tert-butoxy)carbonylamino]-3-[3,4-bis(phenylmethoxy) phenyl]propanoate. $^1$H NMR (400 MHz, CDCl$_3$): δ 1.08 (d, J=6.4 Hz, 3H), 1.11 (d, J=6.4 Hz, 3H), 1.41 (s, 9H), 2.96 (m, 2H), 3.66 (s, br, 1H), 4.34 (m, 1H), 4.75 (m, 1H), 4.98 (m, 1H), 5.10 (s, 4H), 6.66 (d, J=8 Hz, 1H), 6.77 (s, 1H), 6.82 (d, J=8 Hz, 1H), 7.26-7.41 (m, 10H).

Step B: (1R,2R)-1-Methyl-2-phenylcarbonyloxypropyl (2S)-2-[(tert-butoxy)carbonylamino]-3-[3,4-bis(phenylmethoxy)phenyl]propanoate To a solution of benzoic acid (0.57 g, 4.8 mmol) in anhydrous dichloromethane was added triethylamine (1.7 mL, 12 mmol), and 2,4,6-trichlorobenzoyl chloride (0.9 mL, 5.76 mmol) were added. The resulting mixture was stirred for 30 min and a solution of (1R,2R)-2-hydroxy-1-methylpropyl (2S)-2-[(tert -butoxy)carbonylamino]-3-[3,4-bis (phenylmethoxy)phenyl]propanoate (2.4 g, 4.4 mmol) in dichloromethane was slowly added to the reaction mixture, followed by the addition of a catalytic amount of 4-(dimethylamino)pyridine. The resulting mixture was stirred at room temperature for 16 hrs, washed with 10% citric acid, dried over Na$_2$SO$_4$, and concentrated. Chromatography (silica gel, 20% ethyl acetate in hexane) of the residue afforded 2.6 g (90%) of (1R,2R)-1-Methyl-2-phenylcarbonyloxypropyl (2S)-2-[(tert -butoxy)carbonylamino]-3-[3,4-bis(phenylmethoxy)phenyl]propanoate. $^1$H NMR (400 MHz, CDCl$_3$): δ 1.26 (d, J=6.4 Hz, 6H), 1.39 (s, 9H), 2.78 (m, 1H), 2.96 (m, 1H), 4.51 (m, 1H), 4.89 (d, 1H), 5.10 (s, 4H), 5.15 (m, 1H), 6.57 (d, J=8 Hz, 1H), 6.71 (s, 1H), 6.77 (d, J=8 Hz, 1H), 7.25-7.43 (m, 12H), 7.52 (t, J=7.6 Hz, 1H), 7.99 (d, J=7.6 Hz, 2H).

Step C: (1R,2R)-1-Methyl-2-phenylcarbonyloxypropyl (2S)-3-(3,4-dihydroxyphenyl)-2-[(tert-butoxy)carbonylamino]propanoate 200 mg of 10% Pd—C pre-mixed with 10 mL of methanol was added to a solution of (1R,2R)-1-methyl-2-phenylcarbonyloxypropyl (2S)-2-[(tert-butoxy)carbonylamino]-3-[3,4-bis(phenylmethoxy)phenyl]propanoate (2.6 g, 3.9 mmol) in 40 mL of tetrahydrofuran under a nitrogen atmosphere. The resulting mixture was stirred under hydrogen at room temperature for 2 hrs. After filtration and washing with methanol, the filtrate was concentrated and chromatography (silica gel, 30% ethyl acetate in hexane) of the residue afforded 1.8 g (95%) of (1R,2R)-1-Methyl-2-phenylcarbonyloxypropyl (2S)-3-(3,4-dihydroxyphenyl)-2-[(tert-butoxy)carbonylamino]propanoate. MS (ESI) m/z 474.31 (M+H)$^+$ and 472.18 (M–H)$^-$.

Step D: (1R,2R)-1-Methyl-2-phenylcarbonyloxypropyl (2S)-2-amino-3-(3,4-dihydroxyphenyl)propanoate hydrochloride (1R,2R)-1-methyl-2-phenylcarbonyloxypropyl (2S)-3-(3,4-dihydroxyphenyl)-2-[(tert-butoxy)carbonylamino]propanoate (1.8 g, 2.7 mmol) was dissolved in 40 mL of 4M HCl in dioxane. The mixture was stirred at room temperature for 30 min. The dioxane was evaporated completely under reduced pressure. The resulting a white solid was dissolved in acetonitrile (5 mL), and ether added until the solution became slightly cloudy. The solution was refrigerated overnight, and the product crystallized. The white crystalline solid was collected and dried under vacuum to afford 1.0 g (87%) of the title compound. $^1$H NMR (400 MHz, CD$_3$OD): δ 1.12 (d, J=6 Hz, 3H), 1.24 (d, J=6 Hz, 3H), 2.85 (dd, J=8, 14 Hz, 1H), 3.02 (dd, J=5.2, 14 Hz, 1H), 4.15 (t, J=5.6 Hz, 1H), 5.06 (m, 2H), 6.46 (dd, J=2, 8 Hz, 1H), 6.61 (d, J=2 Hz, 1H), 6.65 (d, J=8 Hz, 1H), 7.54 (t, J=7.6 Hz, 2H), 7.65 (t, J=7.6 Hz, 1H), 7.90 (m, 2H). MS (ESI) m/z 374.11 (M+H)$^+$ and 372.08 (M–H)$^-$.

Example 17

(1S,2S)-1-Methyl-2-phenylcarbonyloxypropyl (2S)-2-amino-3-(3,4-dihydroxyphenyl)propanoate hydrochloride Following the procedure described in Example 16, and substituting (2R,3R)-(–)-2,3-butanoldiol with (2S,3S)-(+)-2,3-butanediol, provided the title compound (34% over 4 steps) as a white solid. $^1$H NMR (400 MHz, CD$_3$OD): δ 1.30 (d, J=6 Hz, 3H), 1.34 (d, J=6 Hz, 3H), 2.68 (dd, J=8, 14.4 Hz, 1H), 2.94 (dd, J=6, 14.4 Hz, 1H), 4.01 (dd, J=5.6, 8 Hz, 1H), 5.20 (m, 2H), 6.44 (dd, J=2, 8 Hz, 1H), 6.59 (d, J=2 Hz, 1H), 6.66 (d, J=8 Hz, 1H), 7.46 (t, J=7.6 Hz, 2H), 7.59 (t, J=7.6 Hz, 1H), 7.99 (m, 2H). MS (ESI) m/z 374.16 (M+H)$^+$ and 372.08 (M–H)$^-$.

Example 18

(1R,2R)-1-Methyl-2-(4-fluorophenylcarbonyloxy)propyl (2S)-2-amino-3-(3,4-dihydroxyphenyl)propanoate hydrochloride Following the procedure described in Example 16, and substituting benzoic acid with 4-fluorobenzoic acid, provided the title compound (42% over 4 steps) as a white solid. $^1$H NMR (400 MHz, CD$_3$OD): δ 1.24 (d, J=6.4 Hz, 3H), 1.32 (d, J=6.4 Hz, 3H), 3.06 (d, J=6.4 Hz, 2H), 4.21 (t, J=6.8 Hz, 1H), 5.19 (m, 2H), 6.57 (dd, J=2, 8 Hz, 1H), 6.71 (d, J=2 Hz, 1H), 6.74 (d, J=8 Hz, 1H), 7.24 (t, J=8.8 Hz, 2H), 8.02 (dd, J=5.2, 8.8 Hz, 2H). MS (ESI) m/z 392.20 (M+H)$^+$ and 390.15 (M–H)$^-$.

Example 19

(1S,2S)-1-Methyl-2-(4-fluorophenylcarbonyloxy)propyl (2S)-2-amino-3-(3,4-dihydroxyphenyl)propanoate hydrochloride Following the procedure described in Example 16, substituting benzoic acid with 4-fluorobenzoic acid and (2R,3R)-(–)-2,3-butanediol with (2S,3S)-(+)-2,3-butanediol separately, provided the title compound (47% over 4 steps) as a white solid.
$^1$H NMR (400 MHz, CD$_3$OD): δ 1.32 (d, J=6 Hz, 3H), 1.36 (d, J=6 Hz, 3H), 2.75 (dd, J=8, 14.4 Hz, 1H), 3.02 (dd, J=5.6, 14.4 Hz, 1H), 4.22 (dd, J=6, 8 Hz, 1H), 5.23 (m, 1H), 6.46 (dd, J=2, 8 Hz, 1H), 6.61 (d, J=2 Hz, 1H), 6.68 (d, J=8 Hz, 1H), 7.19 (t, J=8.4 Hz, 2H), 8.05 (dd, J=5.2, 8.4 Hz, 2H). MS (ESI) m/z 392.15 (M+H)$^+$ and 390.10 (M–H)$^-$.

Example 20

3-(4-Methoxyphenylcarbonyloxy)propyl (2S)-2-amino-3-(3,4-dihydroxyphenyl)propanoate hydrochloride Step A: 3-Bromopropyl 4-methoxybenzoate 1-(3-dimethylaminopropyl)-3-ethylcarbodiimide hydrochloride (EDAC) (3.4 g, 17.7 mmol) was slowly added to a solution of 4-methoxybenzoic acid (2.0 g, 13.1 mmol), 3-bromopropan-1-ol (1.1 mL, 12.6 mmol), and 4-(dimethylamino)pyridine (100 mg) in 80 mL of anhydrous dichloromethane. The mixture was stirred at room temperature for 16 hrs. The reaction mixture was diluted with dichloromethane and washed with 0.5N HCl twice, followed by the addition of saturated NaHCO$_3$ solution and brine. The organic layer was dried through MgSO$_4$ and concentrated under reduced pressure. Chromatography (silica gel, 1:10 ethyl acetate/hexane) of the residue afforded 2.1 g (61%) of 3-Bromopropyl 4-methoxybenzoate.

Step B: 3-(4-Methoxyphenylcarbonyloxy)propyl (2S)-2-amino-3-(3,4-dihydroxyphenyl)propanoate hydrochloride A suspension of 3-bromopropyl 4-methoxybenzoate (2.1 g, 7.7 mmol), (2S)-3-(3,4-dihydroxyphenyl)-2-[(tert-butoxy)carbonylamino]propanoic acid (3.43 g, 11.5 mmol), and cesium bicarbonate (2.98 g, 15.4 mmol) in 1-methyl-2-pyrrolidinone (40 mL) was stirred at 50° C. for 3 hrs. The reaction mixture was diluted with ether and washed with water three times followed by brine. The organic layer was separated, dried through a MgSO₄ pad and concentrated under reduced pressure. Chromatography (silica gel, 1:1 ethyl acetate/hexane) of the residue provided 3.7 g (98%) of a clear viscous oil. The oil was treated with 4.0 MHCl in 1,4-dioxane at room temperature for 30 min. The reaction mixture was concentrated to dryness under reduced pressure. The resulting viscous oil was purified by prep-HPLC. The HPLC fractions were pooled, treated with 20 mL of 0.5N HCl, and dried by lyophilization to yield 1.3 g (41%) of the title compound as a white solid. $^1$H NMR (400 MHz, D₂O): δ 1.98-2.16 (m, 2H), 2.91 (dd, J=7.4, 15.0 Hz, 1H), 2.97 (dd, J=6.4, 15.2 Hz, 1H), 3.79 (s, 3H), 4.20 (t, J=6.8 Hz, 1H), 4.26 (t, J=5.8 Hz, 2H), 4.29-4.40 (m, 2H), 6.47 (dd, J=2.2, 8.2 Hz, 1H), 6.60 (d, J=2.0 Hz, 1H), 6.72 (d, J=8.0 Hz, 1H), 6.91 (d, J=8.8 Hz, 2H), 7.87 (d, J=8.8 Hz, 2H); MS (ESI) m/z 390.17 (M+H)⁺.

Example 21

3-(2-Hydroxyphenylcarbonyloxy)propyl (2S)-2-amino-3-(3,4-dihydroxyphenyl)propanoate hydrochloride Step A: 3-Bromopropyl 2-(phenylmethoxy)benzoate To a solution of 2-(phenylmethoxy)benzoic acid (1.0 g, 4.4 mmol), 3-bromopropan-1-ol (0.35 mL, 4.0 mmol), and 4-(dimethylamino)pyridine (50 mg) in 20 mL of anhydrous dichloromethane, 1-(3-dimethylaminopropyl)₃-ethylcarbodiimide hydrochloride (EDAC) (1.3 g, 6.6 mmol) was slowly added. The resulting mixture was stirred at room temperature for 16 hrs. The reaction mixture was diluted with dichloromethane and washed with 0.5N HCl three times followed by the addition of a saturated NaHCO₃ solution and brine. The organic layer was separated, dried through a MgSO₄ pad, and concentrated under reduced pressure. Chromatography (silica gel, 1:9 ethyl acetate/hexane) of the residue afforded 0.8 g (58%) of 3-Bromopropyl 2-(phenylmethoxy)benzoate.

Step B: 3-(2-Hydroxyphenylcarbonyloxy)propyl (2S)-2-amino-3-(3,4-dihydroxyphenyl)propanoate hydrochloride A suspension of 3-bromopropyl 2-(phenylmethoxy)benzoate (0.8 g, 2.3 mmol), (2S)-3-(3,4-dihydroxyphenyl)-2-[(tert-butoxy)carbonylamino]propanoic acid (1.0 g, 3.4 mmol), and cesium bicarbonate (0.89 g, 4.6 mmol) in 1-methyl-2-pyrrolidinone (15 mL) was stirred at 50° C. for 3 hrs. The reaction mixture was diluted with ether and washed with water twice followed by brine. The organic layer was dried through MgSO₄ and concentrated under reduced pressure. Chromatography (silica gel, 1:1 ethyl acetate/hexane) of the residue gave 1.2 g (93%) of a clear viscous oil. To the solution of the oil in THF was added 300 mg of 10% Pd/C. The air in the flask was removed under vacuum and replaced with 1 atm H₂. The suspension was stirred under H₂ at room temperature overnight. The reaction mixture was filtered through a Celite pad. The solvent was removed under vacuum. The resulting viscous oil was treated with 4.0 MHCl in 1,4-dioxane at room temperature for 30 min. The reaction mixture was concentrated to dryness under reduced pressure and purified by prep-HPLC. The HPLC fractions were pooled, treated with 10 mL of 0.5NHCl, and dried by lyophilization to yield 545 mg (68%) of the title compound as a white solid. $^1$H NMR (400 MHz, D₂O): δ 1.86-2.10 (m, 2H), 2.91 (dd, J=7.0, 14.6 Hz, 1H), 2.96 (dd, J=6.6, 15.0 Hz, 1H), 4.08-4.20 (m, 2H), 4.19 (t, J=6.8 Hz, 1H), 4.26 (t, J=5.8 Hz, 2H), 6.42 (dd, J=2.2, 8.2 Hz, 1H), 6.58 (d, J=2.0 Hz, 1H), 6.67 (d, J=8.4 Hz, 1H), 6.78 (t, J=7.6 Hz, 1H), 6.80 (d, J=8.0 Hz, 1H), 7.36 (dt, J=1.4, 7.2 Hz, 1H), 7.59 (dd, J=1.2, 8.0 Hz, 1H); MS (ESI) m/z 376.08 (M+H)⁺.

Example 22

3-(4-Hydroxyphenylcarbonyloxy)propyl (2S)-2-amino-3-(3,4-dihydroxyphenyl)propanoate hydrochloride Following the procedure described in Example 21, and substituting 2-(phenylmethoxy)benzoic acid with 4-(phenylmethoxy)benzoic acid, provided the title compound as a white solid (41% over two steps). $^1$H NMR (400 MHz, D₂O): δ 1.94-2.14 (m, 2H), 2.99 (dd, J=6.4, 14.8 Hz, 1H), 2.95 (dd, J=7.2, 14.4 Hz, 1H), 4.12-4.28 (m, 3H), 4.32 (t, J=5.8 Hz, 2H), 6.47 (dd, J=2.0, 8.0 Hz, 1H), 6.61 (d, J=2.0 Hz, 1H), 6.72 (d, J=8.4 Hz, 1H), 6.83 (d, J=8.8 Hz, 2H), 7.80 (d, J=8.8 Hz, 2H); MS (ESI) m/z 376.08 (M+H)⁺.

Example 23

2-Hydroxy-3-phenylcarbonyloxypropyl (2S)-2-amino-3-(3,4-dihydroxyphenyl)propanoate hydrochloride Step A: Oxiran-2-ylmethyl benzoate Benzoyl chloride (1.2 mL, 10.0 mmol) was added to a solution of glycidol (0.67 mL, 10.0 mmol) and pyridine (0.81 mL, 10.0 mmol) in anhydrous dichloromethane at 0° C. The reaction mixture was further stirred at 0° C. for 60 min. The reaction mixture was then concentrated to dryness under reduced pressure, diluted with ethyl acetate, and washed with 10% citric acid twice followed by the addition of a saturated NaHCO₃ solution and brine. The organic phase was dried over MgSO₄ and concentrated to dryness to yield 1.8 g (100%) of Oxiran-2-ylmethyl benzoate.

Step B: 2-Hydroxy-3-phenylcarbonyloxypropyl (2S)-3-(3,4-dihydroxyphenyl)-2-[(tert-butoxy)carbonylamino]propanoate A solution of oxiran-2-ylmethyl benzoate (3.0 g, 16.8 mmol), (2S)-3-(3,4-dihydroxyphenyl)-2-[(tert-butoxy)carbonylamino]propanoic acid (6.0 g, 20.2 mmol), and tetrabutylammonium bromide (542 mg, 1.7 mmol) in anhydrous toluene was heated to 90° C. for 18 hrs. The reaction mixture was concentrated to dryness under reduced pressure, diluted with ethyl acetate, and washed with water twice followed by the addition of a saturated NaHCO₃ solution and brine. The organic layer was dried through MgSO₄ and concentrated under reduced pressure. Chromatography (silica gel, 1:1 ethyl acetate/hexane) of the residue afforded 2.05 g (26%) of 2-Hydroxy-3-phenylcarbonyloxypropyl (2S)-3-(3,4-dihydroxyphenyl)-2-[(tert-butoxy)carbonylamino]propanoate.

Step C: 2-Hydroxy-3-phenylcarbonyloxypropyl (2S)-2-amino-3-(3,4-dihydroxyphenyl)propanoate hydrochloride 2-Hydroxy-3-phenylcarbonyloxypropyl (2S)-3-(3,4-dihydroxyphenyl)-2-[(tert-butoxy)carbonylamino]propanoate (2.05 g, 4.3 mmol) was treated with 4.0 MHCl in 1,4- dioxane at room temperature for 30 min. The reaction mixture was concentrated to dryness under reduced pressure and purified by prep-HPLC. The HPLC fractions were pooled, treated with 10 mL of 0.5NHCl, and dried by lyophilization to yield 0.85 g (48%) of the title compound as a white solid. $^1$H NMR (400 MHz, D$_2$O): δ 3.11 (t, J=6.6 Hz, 2H), 4.38-4.44 (m, 6H), 6.60 (dd, J=2.2, 7.8 Hz, 1/2H), 6.61 (dd, J=2.4, 8.0 Hz, 1/2H), 6.70 (d, J=2.0 Hz, 1/2H), 6.71 (d, J=2.0 Hz, 1/2H), 6.77 (d, J=8.0 Hz, 1/2H), 6.78 (d, J=8.0 Hz, 1/2H), 7.46-7.52 (m, 2H), 7.60-7.68 (m, 1H), 7.96-8.02 (m, 2H); MS (ESI) m/z 376.15 (M+H)$^+$.

Example 24

(2R)-2-(2-Hydroxyphenylcarbonyloxy)propyl (2S)-2-amino-3-(3,4-dihydroxyphenyl)propanoate hydrochloride Step A:
(2R)-1-(tert-Butyldimethylsiloxy)propan-2-ol A solution of tert-butyldimethylchlorosilane (9.9 g, 65.7 mmol) in dichloromethane was added dropwise to a solution of (R)-(−)-1,2-propanediol (5 g, 65.7 mmol) and imidazole (4.47 g, 65.7 mmol) in anhydrous dichloromethane at 0° C. The reaction mixture was stirred at 0° C. for 30 min before dilution with dichloromethane. The solution was washed with water three times followed by the addition of brine. The organic layer was separated, dried through a MgSO$_4$ pad and concentrated under reduced pressure to afford 12.0 g (96%) of (2R)-1-(tert-Butyldimethylsiloxy)propan-2-ol.

Step B: (1R)-1-Methyl-2-(tert-butyldimethylsiloxy)ethyl 2-(phenylmethoxy)benzoate To a solution of 2-(phenylmethoxy)benzoic acid (4.0 g, 17.5 mmol), (2R)-1-(tert-butyldimethylsiloxy)propan-2-ol (2.78 g, 14.6 mmol), and 4-(dimethylamino)pyridine (183 mg) in 100 mL of anhydrous dichloromethane, 1-(3-dimethylaminopropyl)3-ethylcarbodiimide hydrochloride (EDAC) (4.2 g, 17.5 mmol) was slowly added. The resulting mixture was stirred at room temperature for 48 hrs. The reaction mixture was diluted with dichloromethane and washed with 0.5N HCl twice followed by the addition of saturated NaHCO$_3$ solution and brine. The organic layer was separated, dried through a MgSO$_4$ pad, and concentrated under reduced pressure. Chromatography (silica gel, 1:12 ethyl acetate/hexane) of the residue afforded 1.7 g (29%) of (1R)-1-Methyl-2-(tert-butyldimethylsiloxy)ethyl 2-(phenylmethoxy)benzoate.

Step C: (1 R)-2-Hydroxy-isopropyl 2-(phenylmethoxy)benzoate

Triethylamine trihydrofluoride (1.7 mL, 10.5 mmol) was added slowly to a solution of (1R)-1-methyl-2-(tert-butyldimethylsiloxy)ethyl 2-(phenylmethoxy)benzoate (1.7 g, 4.24 mmol) in anhydrous tetrahydrofuran. The mixture was stirred at room temperature for 48 hrs. The solvent was removed under reduced pressure. The reaction mixture was diluted with dichloromethane and washed with saturated NaHCO$_3$ solution twice followed by the addition of brine. The organic layer was dried through MgSO$_4$ and concentrated under reduced pressure. Chromatography (silica gel, 1:5 ethyl acetate/hexane) of the residue afforded 1.5 g (100%) of (1R)-2-Hydroxy-isopropyl 2-(phenylmethoxy)benzoate.

Step D: (2R)-2-[2-(phenylmethyloxy)phenylcarbonyloxy]propyl (2S)-2-[(tert-butoxy)carbonylamino]-3-[3,4-bis(phenylmethyloxy)phenyl]propanoate 1-(3-dimethylaminopropyl)$_3$-ethylcarbodiimide hydrochloride (EDAC) (1.5 g, 7.86 mmol) was slowly added to a solution of (2S)-2-[(tert-butoxy)carbonylamino]-3-[3,4-bis(phenylmethoxy)phenyl]propanoic acid (2.75 g, 5.76 mmol), (1R)-2-hydroxy-isopropyl 2-(phenylmethoxy)benzoate (1.5 g, 5.24 mmol), and 4-(dimethylamino)pyridine (64 mg) in 40 mL of anhydrous dichloromethane. The resulting mixture was stirred at room temperature for 16 hrs. The reaction mixture was diluted with dichloromethane and washed with 0.5N HCl twice followed by the addition of saturated NaHCO$_3$ solution and brine. The organic layer was separated, dried through a MgSO$_4$ pad and concentrated under reduced pressure. Chromatography (silica gel, 1:3 ethyl acetate/hexane) of the residue afforded 3.5 g (90%) of (2R)-2-[2-(phenylmethyloxy)phenylcarbonyloxy]propyl (2S)-2-[(tert-butoxy)carbonylamino]-3-[3,4-bis(phenylmethyloxy)phenyl]propanoate.

Step E: (2R)-2-(2-Hydroxyphenylcarbonyloxy)propyl (2S)-2-amino-3-(3,4-dihydroxyphenyl)propanoate hydrochloride 1.0 g of 10% Pd/C was added to a solution of (2R)-2-[2-(phenylmethyloxy)phenylcarbonyloxy]propyl (2S)-2-[(1,1-dimethylethyloxy)carbonylamino]-3-[3,4 bis(phenylmethyloxy)phenyl]propanoate (3.5 g, 4.69 mmol) in THF. The air in the flask was removed under vacuum and replaced with 1 atm H$_2$. The suspension was stirred under H$_2$ at room temperature overnight. The reaction mixture was filtered through a Celite pad. The solvent was removed under vacuum. The resulting viscous oil was treated with 4.0M HCl in 1,4-dioxane at room temperature for 30 min. The reaction mixture was concentrated to dryness under reduced pressure and purified by prep-HPLC. The HPLC fractions were pooled, treated with 10 mL of 0.5N HCl, and dried by lyophilization to yield 1.2 g (62%) of the title compound as a white solid. $^1$H NMR (400 MHz, D$_2$O): δ 1.30 (d, J=6.4 Hz, 3H), 2.97 (dd, J=6.6, 14.2 Hz, 1H), 3.02 (dd, J=6.2, 14.2 Hz, 1H), 4.27 (dd, J=6.6, 12.2 Hz, 1H), 4.30 (t, J=7.0 Hz, 1H), 4.49 (dd, J=2.8, 12.0 Hz, 1H), 5.22 (doublet of pentets, J=2.4, 6.4 Hz, 1H), 6.47 (dd, J=2.2, 8.2 Hz, 1H), 6.62 (d, J=2.0 Hz, 1H), 6.63 (d, J=8.4 Hz, 1H), 6.81 (t, J=7.6 Hz, 1H), 6.85 (d, J=8.4 Hz, 1H), 7.39 (dt, J=1.6, 7.0 Hz, 1H), 7.62 (dd, J=1.4, 7.8 Hz, 1H); MS (ESD m/z 376.15 (M+H)$^+$.

Example 25

(2 R)-2-(4-Hydroxyphenylcarbonyloxy)propyl (2S)-2-amino-3-(3,4-dihydroxyphenyl)propanoate hydrochloride Following the procedure described in Example 24, and substituting 2-(phenylmethoxy)benzoic acid with 4-(phenylmethoxy)benzoic acid, provided the title compound (14% over five steps). $^1$H NMR (400 MHz, D$_2$O): δ 1.26 (d, J=6.4 Hz, 3H), 2.95 (dd, J=7.0, 14.6 Hz, 1H), 3.01 (dd, J=6.6, 14.6 Hz, 1H), 4.24 (dd, J=6.4, 12.0 Hz, 1H), 4.27 (t, J=6.6 Hz, 1H), 4.45 (dd, J=3.0, 11.8 Hz, 1H), 5.16 (doublet of pentets, J=2.4, 6.4 Hz, 1H), 6.45 (dd, J=2.0, 8.0 Hz, 1H), 6.61 (d, J=2.0 Hz, 1H), 6.63 (d, J=8.0 Hz, 1H), 6.78 (d, J=8.8 Hz, 2H), 7.70 (d, J=8.8 Hz, 2H); MS (ESI) m/z 376.15 (M+H)$^+$.

Example 26

(2 R)-2-(4-Methoxyphenylcarbonyloxy)propyl (2S)-2-amino-3-(3,4-dihydroxyphenyl)propanoate hydrochloride Following the procedure described in Example 24, and substituting 2-(phenylmethoxy)benzoic acid with 4-methoxybenzoic acid, provided the title compound as a white solid (32% over five steps). $^1$H NMR (400 MHz, D$_2$O): δ 1.26 (d, J=6.8 Hz, 3H), 2.91 (dd, J=7.4, 14.6 Hz, 1H), 2.98 (dd, J=6.2, 14.6 Hz, 1H), 3.64 (s, 3H), 4.22 (dd, J=6.4, 12.0 Hz, 1H), 4.27 (t, J=6.8 Hz, 1H), 4.47 (dd, J=2.6, 11.8 Hz, 1H), 5.17 (doublet of pentets, J=2.8, 6.4 Hz, 1H), 6.41 (dd, J=2.0, 8.4 Hz, 1H), 6.60 (d, J=2.4 Hz, 1H), 6.61 (d, J=8.0 Hz, 1H), 6.69 (d, J=8.8 Hz, 2H), 7.65 (d, J=8.8 Hz, 2H); MS (ESI) m/z 390.32 (M+H)$^+$.

Example 27

2-[(2-Hydroxyphenyl)carbonylamino]ethyl (2S)-2-amino-3-(3,4-dihydroxyvphenyl)propanoate hydrochloride

Step A: N-(2-Hydroxyethyl)[2-(phenylmethoxy)phenyl]carboxamide 1-(3-dimethylaminopropyl)$_3$-ethylcarbodiimide hydrochloride (EDAC) (1.3 g, 6.57 mmol) was slowly added to a solution of 2-(phenylmethoxy)benzoic acid (1.5 g, 6.57 mmol), 1-hydroxybenzotriazole (HOBt) (0.89 g, 6.57 mmol), and ethanolamine (0.40 mL, 6.57 mmol) in 50 mL of anhydrous THF at 0° C. The suspension was stirred and warmed up slowly to room temperature over 24 hrs. The reaction mixture was concentrated to dryness under reduced pressure and the resulting residue was diluted with dichloromethane and washed with 0.5N HCl twice followed by the addition of a saturated NaHCO$_3$ solution and brine. The organic layer was separated, dried through a MgSO$_4$ pad and concentrated under reduced pressure to afford 1.8 g (100%) of N-(2-Hydroxyethyl)[2-(phenylmethoxy)phenyl]carboxamide.

Step B: 2-{[2-(Phenylmethoxy)phenyl]carbonylamino}ethyl (2S)-2-[(tert-butoxy)carbonylamino]-3-[3,4-bis(phenylmethoxy)phenyl]propanoate To a solution of (2 S)-2-[(tert-butoxy)carbonylamino]-3-[3,4-bis(phenylmethoxy)phenyl]propanoic acid (3.95 g, 8.27 mmol), N-(2-hydroxyethyl)[2-(phenylmethoxy)phenyl]carboxamide (1.8 g, 6.63 mmol), and 4-(dimethylamino)pyridine (84 mg) in 40 mL of anhydrous dichloromethane was added slowly 1-(3-dimethylaminopropyl)3-ethylcarbodiimide hydrochloride (EDAC) (2.0 g, 10.34 mmol) was slowly added. The resulting mixture was stirred at room temperature for 16 hrs. The reaction mixture was diluted with dichloromethane and washed with 0.5N HCl twice followed by the addition of brine. The organic layer was separated, dried through MgSO$_4$ and concentrated under reduced pressure. Chromatography (silica gel, 1:2 then 1:1.5 ethyl acetate/hexane) of the residue afforded 3.7 g (73%) of 2-{[2-(Phenylmethoxy)phenyl]carbonylamino}ethyl (2S)-2-[(tert-butoxy)carbonylamino]-3-[3,4-bis(phenylmethoxy)phenyl]propanoate.

Step C: 2-[(2-Hydroxyphenyl)carbonylamino]ethyl (2S)-2-amino-3-(3,4-dihydroxyphenyl)propanoate hydrochloride To a solution of 2-{[2-(phenylmethoxy)phenyl]carbonylamino}ethyl (2S)-2-[(tert-butoxy)carbonylamino]-3-[3,4-bis(phenylmethoxy)phenyl]propanoate (3.7 g, 5.06 mmol) in THF was added 1.0 g of 10% Pd/C. The air in the flask was removed under vacuum and replaced with 1 atm H$_2$. The suspension was stirred under H$_2$ at room temperature overnight. The reaction mixture was filtered through a Celite pad. The solvent was removed under vacuum. The resulting viscous oil was treated with 4.0M HCl in 1,4-dioxane at room temperature for 30 min. The reaction mixture was concentrated to dryness under reduced pressure and purified by prep-HPLC. The HPLC fractions were pooled, treated with 15 mL of 0.5N HCl, and dried by lyophilization to yield 1.2 g (61%) of the title compound as a white solid. $^1$H NMR (400 MHz, D$_2$O): δ 2.86 (dd, J=6.8, 14.8 Hz, 1H), 2.91 (dd, J=6.0, 14.8 Hz, 1H), 3.38-3.62 (m, 2H), 4.14-4.30 (m, 2H), 4.19 (t, J=6.6 Hz, 1H), 6.34 (dd, J=2.2, 8.2 Hz, 1H), 6.49 (d, J=2.0 Hz, 1H), 6.52 (d, J=8.0 Hz, 1H), 6.70 (dd, J=0.8, 8.4 Hz, 1H), 6.73 (dt, J=1.2, 7.8 Hz, 1H), 7.18 (ddd, J=1.6, 7.2, 7.4 Hz, 1H), 7.42 (dd, J=1.6, 8.0 Hz, 1H); MS (ESI) m/z 361.28 (M+H)$^+$.

Example 28

2(R)- and 2(S)-(3-Pyridylcarbonyloxy)propyl (2S)-2-amino-3-(3,4-dihydroxyphenyl)propanoates

Step A: 1-Bromoisopropyl nicotinate

Nicotinic acid chloride (2.56 g, 20 mmol) and 30 mg of DMAP were added to a mixture of 2-bromo-2-propanol (2.8 g, 20 mmol), triethylamine (5.6 mL, 20 mmol) in dichloromethane at 0° C. The resulting mixture was stirred at room temperature overnight. The product was partitioned between ethyl acetate and water. The organic phase was separated, dried over MgSO$_4$, and concentrated to yield 1-Bromoisopropyl nicotinate, which was used in the next reaction without further purification.

Step B: (2S)-2-[(tert-butoxy)carbonylamino]-3-[3,4-bis(phenylmethoxy)phenyl]propionic acid cesium salt Cesium hydrogencarbonate (194 mg, 1 mmol) was added to a solution of (2S)-2-[(tert-butoxy)carbonylamino]-3-[3,4-bis(phenylmethoxy)phenyl]propionic acid (297 mg, 1 mmol) in 5 mL water and 5 mL acetonitrile. The resulting mixture was stirred at room temperature for 10 minutes, then frozen and lyophilized to yield (2S)-2-[(tert-butoxy)carbonylamino]-3-[3,4-bis(phenylmethoxy)phenyl]propionic acid cesium salt as a white solid, which was used in the next reaction without further purification.

Step C: 2(R)- and 2(S)-(3-Pyridylcarbonyloxy)propyl (2S)-2-amino-3-(3,4-dihydroxyphenyl)propanoates 1-Bromoisopropyl nicotinate (366 mg, 1.5 mmol) was added to a solution of (2S)-2-[(tert-butoxy)carbonylamino]-3-[3,4-bis(phenylmethoxy)phenyl]propionic acid cesium salt (432 mg, 1 mmol) in dimethylacetamide at room temperature and the mixture stirred at 55° C. for 16 hrs. After removing the solvent under reduced pressure, the residue was partitioned between ethyl acetate and water. The organic phase was separated, dried over MgSO$_4$, and concentrated. The resulting residue was treated with 30% trifluoroacetic acid in dichloromethane at room temperature for 30 min. After removing the solvent, the resulting residue was purified by reverse phase preparative HPLC to afford 180 mg of the title compounds as a mixture of two diastereoisomers. MS (ESI) m/z 362.22 (M+H)$^+$.

Example 29

2(R)- and 2(S)-(4-Pyridylcarbonyloxy)propyl (2S)-2-amino-3-(3,4-dihydroxyphenyl)propanoates Following the procedure described in Example 28, and substituting nicotinic acid chloride with isonicotinic acid chloride, provided the title compounds as a mixture of two diastereoisomers. MS (ESI) m/z 362.13 (M+H)$^+$.

Example 30

2(R)- and 2(S)-(2-Ethoxy-3-pyridylcarbonyloxy) propyl (2S)-2-amino-3-(3,4-dihydroxyphenyl)propanoates Following the procedure described in Example 28, and substituting nicotinic acid chloride with 1'-ethoxynicotinic acid chloride, provided the title compounds as a mixture of two diastereoisomers. MS (ESI) m/z 406.15 (M+H)$^+$.

Example 31

2(R)- and 2(S)-(2-Methyl-5-pyridylcarbonyloxy) propyl (2S)-2-amino-3-(3,4-dihydroxyphenyl)propanoates Following the procedure described in Example 28, and substituting nicotinic acid chloride with 6'-methylnicotinic acid chloride, provided the title compounds as a mixture of two diastereoisomers. MS (ESI) m/z 376.31 (M+H)$^+$.

Example 32

Uptake of Levodopa Prodrugs Following Administration of Levodopa Prodrugs and Carbidopa in Rats Sustained release oral dosage forms, which release drug slowly over periods of 6 to 24 hours, generally release a significant proportion of the dose within the colon. Thus, drugs suitable for use in such dosage forms can exhibit good colonic absorption. This experiment was conducted to assess the uptake and resultant blood levels of levodopa, following intracolonic administration of levodopa prodrugs with coadministration of carbidopa (intracolonically, intraperitoneally or orally), and thereby determine the suitability of levodopa prodrugs for use in an oral sustained release dosage form. Bioavailability of levodopafollowing coadminstration of levodopa prodrugs and carbidopa was calculated relative to oral coadministration of levodopa and carbidopa.

Step A: Administration Protocol

Rats were obtained commercially and were pre-cannulated in the both the ascending colon and the jugular vein. Animals were conscious at the time of the experiment. All animals were fasted overnight and until 4 hours post-dosing of levodopa produg. Carbidopa was administered as a solution in water or citrate buffer either orally, or intraperitoneally or intracolonically at a dose equivalent to 25 mg of carbidopa per kg. Either at the same time or 1 hour after carbidopa dosing, levodopa HCl salt or levodopa prodrug HCl salt was administered as a solution (in water) directly into the colon via the cannula at a dose equivalent to 75 mg of levodopa per kg. Blood samples (0.3 mL) were obtained from the jugular cannula at intervals over 8 hours and were quenched immediately by addition of sodium metabisulfite to prevent oxidation of levodopa. Blood was then further quenched with methanol/perchloric acid to prevent hydrolysis of the levodopa prodrug. Blood samples were analyzed as described below.

Step B: Sample Preparation for Colonically Absorbed Drug

1. In blank 1.5 mL tubes, 300 µL of methanol/perchloric acid was added.

2. Rat blood (300 µL) was collected at different times into EDTA tubes containing 75 µL of sodium metabisulfite, and vortexed to mix. A fixed volume of blood (100 µL) was immediately added into the Eppendorf tube and vortexed to mix.

3. Ten microliters of an levodopa standard stock solution (0.04, 0.2, 1, 5, 25, 100 µg/mL) and 10 µL of the 10% sodium metabisulfate was added to 80 µL of blank rat blood to make up a final calibration standard (0.004, 0.02, 0.1, 0.5, 2.5, 10 µg/mL). Then 300 µL of 50/50 methanol/perchloric acid was added into each tube followed by 20 µL of p-chlorophenylalanine.

4. Samples were vortexed and centrifuged at 14,000 rpm for 10 min.

5. Supernatant was analyzed by LC/MS/MS.

Step C: LC/MS/MS Analysis

An API 4000 LC/MS/MS spectrometer equipped with Agilent 1100 binary pumps and a CTC HTS-PAL autosampler were used in the analysis. A Zorbax XDB C8-4.6×150 mm column was used during the analysis. The mobile phase was 0.1% formic acid (A) and acetonitrile with 0.1% formic acid (B). The gradient condition was: 5% B for 0.5 min, then to 98% B in 3 min, then maintained at 98% B for 2.5 min. The mobile phase was returned to 2% B for 2 min. A TurboIonSpray source was used on the API 4000. The analysis was done in positive ion mode and the MRM transition for each analyte was optimized using standard solution. 5 µL of the samples were injected. Non-compartmental analysis was performed using WinNonlin (v.3.1 Professional Version, Pharsight Corporation, Mountain View, Calif.) on individual animal profiles. Summary statistics on major parameter estimates was performed for $C_{max}$ (peak observed concentration following dosing), $T_{max}$ (time to maximum concentration is the time at which the peak concentration was observed), $AUC_{(0-t)}$ (area under the serum concentration-time curve from time zero to last collection time, estimated using the log-linear trapezoidal method), $AUC_{(0-\infty)}$, (area under the serum concentration time curve from time zero to infinity, estimated using the log-linear trapezoidal method to the last collection time with extrapolation to infinity), and $t_{1/2,z}$ (terminal half-life). Maximum concentrations of levodopa in the blood ($C_{max}$ values) and the area under blood concentration versus time curve (AUC) values after intracolonic dosing of levodopa prodrugs with carbidopa were significantly higher (>2-fold) than those achieved for colonic administration of levodopa with carbidopa.

Intracolonic coadministration of levodopa and carbidopa results in very low relative bioavailability of levodopa (i.e., only 3% of orally coadministered levodopa and carbidopa). By comparison, coadministration of the levodopa prodrugs listed below with carbidopa exhibited improved relative bioavailability of levodopa by at least 2-fold. The range of improved relative bioavailability of levodopa was between 2 and 20 fold. These data demonstrate that certain levodopa prodrugs can be formulated as compositions suitable for effective sustained oral release and uptake of levodopa from the colon.

Levodopa prodrugs which, when administered, produced a relative bioavailability of levodopa at least 2-fold greater than the bioavailability of levodopa produced following the administration of levodopa include:

(2R)-2-Phenylcarbonyloxypropyl (2S)-2-amino-3-(3,4-dihydroxyphenyl)propanoate hydrochloride;
(2R)-2-(4-Methoxyphenylcarbonyloxy)propyl (2S)-2-amino-3-(3,4-dihydroxyphenyl)propanoate hydrochloride;
(2R)-2-(4-Hydroxyphenylcarbonyloxy)propyl (2S)-2-amino-3-(3,4-dihydroxyphenyl)propanoate hydrochloride;
(2R)-2-(2-Hydroxyphenylcarbonyloxy)propyl (2S)-2-amino-3-(3,4-dihydroxyphenyl)propanoate hydrochloride;
2-Hydroxy-3-phenylcarbonyloxypropyl (2S)-2-amino-3-(3,4-dihydroxyphenyl)propanoate hydrochloride;
3-(4-Hydroxyphenylcarbonyloxy)propyl (2S)-2-amino-3-(3,4-dihydroxyphenyl)propanoate hydrochloride;
3-(4-Methoxyphenylcarbonyloxy)propyl (2S)-2-amino-3-(3,4-dihydroxyphenyl)propanoate hydrochloride;
(1R,2R)-1-Methyl-2-(4-fluorophenylcarbonyloxy)propyl (2S)-2-amino-3-(3,4-dihydroxyphenyl)propanoate hydrochloride;
(1S,2S)-1-Methyl-2-phenylcarbonyloxypropyl (2S)-2-amino-3-(3,4-dihydroxyphenyl)propanoate hydrochloride;
(1R)-1-Methyl-2-(4-fluorophenylcarbonyloxy)ethyl (2S)-2-amino-3-(3,4-dihydroxyphenyl)propanoate hydrochloride;
(1S)-1-Methyl-2-phenylcarbonyloxyethyl (2S)-2-amino-3-(3,4-dihydroxyphenyl)propanoate hydrochloride;
(2S)-2-(4-Fluorophenylcarbonyloxy)propyl (2S)-2-amino-3-(3,4-dihydroxyphenyl)propanoate hydrochloride;
(2R)-2-(4-Fluorophenylcarbonyloxy)propyl (2S)-2-amino-3-(3,4-dihydroxyphenyl)propanoate hydrochloride;
(2S)-2-Phenylcarbonyloxypropyl (2S)-2-amino-3-(3,4-dihydroxyphenyl)propanoate hydrochloride;
2-Phenylcarbonyloxyethyl (2S)-2-amino-3-(3,4-dihydroxyphenyl)propanoate hydrochloride; and
(1R)-1-Methyl-2-phenylcarbonyloxyethyl (2S)-2-amino-3-(3,4-dihydroxyphenyl)propanoate hydrochloride.

What is claimed is:

1. A compound of Formula (I):

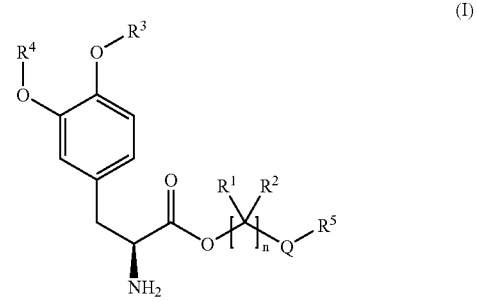

a stereoisomer thereof, an enantiomer thereof, a pharmaceutically acceptable salt thereof, a hydrate thereof, or a solvate of any of the foregoing, wherein Q is —X—CO—;

X is selected from —O—, and —NH—;

n is an integer from 2 to 4;

each $R^1$ and $R^2$ is independently selected from hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, halo, heteroalkyl, substituted heteroalkyl, heteroaryl, substituted heteroaryl, heteroarylalkyl, and substituted heteroarylalkyl;

$R^3$ and $R^4$ are independently selected from hydrogen, —C(O)O$R^7$, —C(O)$R^7$, and —(C$R^8R^9$)OC(O)$R^{10}$;

$R^5$ is selected from hydrogen, alkyl, substituted alkyl, aryl, substituted aryl, arylalkyl, substituted arylalkyl, cycloalkyl, substituted cycloalkyl, heteroalkyl, substituted heteroalkyl, cycloheteroalkyl, substituted cycloheteroalkyl, heteroaryl, substituted heteroaryl, heteroarylalkyl, and substituted heteroarylalkyl; and when Q is —X—CO—, $R^5$ is further selected from alkoxy, substituted alkoxy, cycloalkoxy, and substituted cycloalkoxy;

$R^7$ is selected from alkyl, substituted alkyl, cycloalkyl, substituted cycloalkyl, cycloheteroalkyl, substituted cycloheteroalkyl, aryl, substituted aryl, arylalkyl, substituted arylalkyl, heteroaryl, substituted heteroaryl, heteroarylalkyl, and substituted heteroarylalkyl;

$R^8$ and $R^9$ are independently selected from hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroaryl, substituted heteroaryl, heteroarylalkyl, and substituted heteroarylalkyl, or optionally, $R^8$ and $R^9$ together with the carbon atom to which $R^8$ and $R^9$ are attached form a cycloalkyl, substituted cycloalkyl, cycloheteroalkyl or substituted cycloheteroalkyl ring; and $R^{10}$ is selected from hydrogen, alkyl, substituted alkyl, aryl, substituted aryl, arylalkyl, substituted arylalkyl, cycloalkyl, substituted cycloalkyl, heteroalkyl, substituted heteroalkyl, cycloheteroalkyl, substituted cycloheteroalkyl, heteroaryl, substituted heteroaryl, heteroarylalkyl, and substituted heteroarylalkyl;

with the proviso that the compound of Formula (I) is not derived from 1,3-dihexadecanoylpropane-1,2,3-triol.

2. A compound according to claim 1, wherein each $R^1$ and $R^2$ is independently selected from hydrogen and phenyl, wherein the phenyl group is optionally substituted with one or more substituents selected from halo, —CN, —NO$_2$, —OH, C$_{1-6}$ alkyl, and C$_{1-6}$ alkoxy.

3. A compound according to claim 1, wherein each $R^1$ and $R^2$ is independently selected from hydrogen, —OH, C$_{1-4}$ alkyl, and substituted C$_{1-4}$ alkyl.

4. A compound according to claim 1, wherein each $R^1$ and $R^2$ is independently selected from hydrogen, —OH, C$_{1-3}$ alkyl, and substituted C$_{1-3}$ alkyl.

5. A compound according to claim 1, wherein each $R^1$ and $R^2$ is hydrogen.

6. A compound according to claim 1, wherein $R^5$ is selected from alkanyl, substituted alkanyl, alkenyl, substituted alkenyl, arylalkanyl, substituted arylalkanyl, arylalkanyl, substituted arylalkenyl, cycloalkanyl, substituted cycloalkanyl, cycloheteroalkanyl, substituted cycloheteroalkanyl, heteroarylalkanyl, and substituted heteroarylalkanyl.

7. A compound according to claim 1, wherein $R^5$ is selected from methyl, ethyl, propyl, isopropyl, butyl, isobutyl, sec-butyl, tert-butyl, pentyl, hexyl, cyclopropyl, cyclobutyl, cyclopentyl, cyclohexyl, benzyl, phenethyl and styryl, wherein the aryl ring of the benzyl or styryl group is optionally substituted with one or more substituents selected from halo, —CN, —NO$_2$, —OH, C$_{1-6}$ alkyl, and C$_{1-6}$ alkoxy.

8. A compound according to claim 1, wherein $R^5$ is selected from aryl, substituted aryl, heteroaryl, and substituted heteroaryl.

9. A compound according to claim 1, wherein $R^5$ is selected from C$_{5-8}$ aryl, and substituted C$_{5-8}$ aryl substituted with one or more substituents selected from halo, —CN, —NO$_2$, —OH, C$_{1-6}$ alkyl, and C$_{1-6}$ alkoxy.

10. A compound according to claim 1, wherein $R^5$ is selected from phenyl and pyridyl which are optionally substituted with halo, —OH, C$_{1-3}$ alkyl, and C$_{1-3}$ alkoxy.

11. A compound according to claim 1, wherein X is —O—.

12. A compound according to claim 1, wherein X is —NH—.

13. A compound according to claim 1, wherein $R^3$ and are independently selected from hydrogen, —C(O)OR$^7$, and —C(O)R$^7$.

14. A compound according to claim 13, wherein $R^7$ is selected from alkanyl, substituted alkanyl, cycloalkanyl, substituted cycloalkanyl, arylalkanyl, substituted arylalkanyl, heteroarylalkanyl, and substituted heteroarylalkanyl.

15. A compound according to claim 13, wherein $R^7$ is selected from methyl, ethyl, propyl, isopropyl, butyl, isobutyl, sec-butyl, tert-butyl, cyclopropyl, cyclobutyl, cyclopentyl, cyclohexyl and benzyl, where the aryl ring of the benzyl group is optionally substituted with one or more substituents selected from halo, —CN, —NO$_2$, —OH, C$_{1-6}$ alkyl, and C$_{1-6}$ alkoxy.

16. A compound according to claim 13, wherein $R^7$ is selected from aryl, substituted aryl, heteroaryl, and substituted heteroaryl.

17. A compound according to claim 13, wherein $R^7$ is selected from C$_{5-8}$ aryl, C$_{5-8}$ substituted aryl, heteroaryl, substituted heteroaryl, C$_{6-10}$ arylalkyl, and substituted C$_{6-10}$ arylalkyl.

18. A compound according to claim 13, wherein $R^7$ is selected from phenyl, pyridyl, furyl, and thienyl, the aromatic rings of which are optionally substituted with one or more substituents selected from halo, —CN, —NO$_2$, —OH, C$_{1-6}$ alkyl, and C$_{1-6}$ alkoxy.

19. A compound according to claim 1, wherein $R^3$ and $R^4$ are independently selected from hydrogen and —(CR$^8$R$^9$)OC(O)R$^{10}$.

20. A compound according to claim 19, wherein $R^{10}$ is selected from hydrogen, C$_{1-10}$ alkyl, substituted C$_{1-10}$ alkyl, C$_{5-8}$ aryl, substituted C$_{5-8}$ aryl, C$_{1-15}$ alkoxy, and substituted C$_{1-15}$ alkoxy.

21. A compound according to claim 19, wherein $R^8$ and $R^9$ are independently selected from hydrogen, C$_{1-16}$ alkyl, substituted C$_{1-16}$ alkyl, C$_{5-8}$ aryl, substituted C$_{5-8}$ aryl, C$_{6-10}$ arylalkyl, and substituted C$_{6-10}$ arylalkyl.

22. A compound according to claim 1, wherein the compound has the structure of Formula (II):

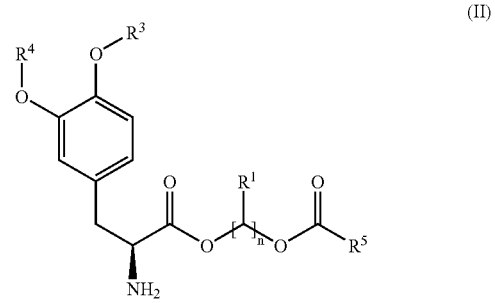

(II)

a stereoisomer thereof, an enantiomer thereof, a pharmaceutically acceptable salt thereof, a hydrate thereof, or a solvate of any of the foregoing, wherein n is an integer from 2 to 4;

$R^1$ is selected from hydrogen, a straight chain C$_{1-3}$ alkyl, and a branched C$_{1-3}$ alkyl; and $R^5$ is selected from phenyl, and substituted phenyl wherein one or more of the substituents is selected from halo, —CN, —NO$_2$, —OH, C$_{1-6}$ alkyl, and C$_{1-6}$ alkoxy.

23. A compound according to claim 22, wherein the compound has the structure:

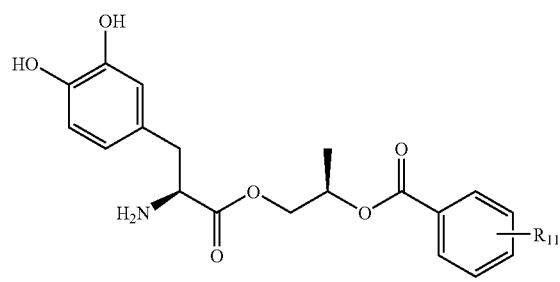

wherein $R^{11}$ is selected from hydrogen, halo, —CN, —NO$_2$, —OH, C$_{1-6}$ alkyl, and C$_{1-6}$ alkoxy.

24. A compound according to claim 22, wherein the compound has the structure:

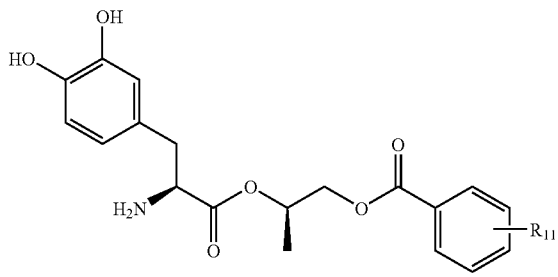

wherein R[11] is selected from hydrogen, halo, —CN, —NO$_2$, —OH, C$_{1-6}$ alkyl, and C$_{1-6}$ alkoxy.

25. A compound according to claim 1, wherein the compound is selected from:
2-Phenylcarbonyloxyethyl (2S)-2-amino-3-(3,4-dihydroxyphenyl)propanoate;
2-(4-Fluorophenylcarbonyloxy)ethyl (2S)-2-amino-3-(3,4-dihydroxyphenyl)propanoate;
3-Phenylcarbonyloxypropyl (2S)-2-amino-3-(3,4-dihydroxyphenyl)propanoate;
3-(4-Fluorophenylcarbonyloxy)propyl (2S)-2-amino-3-(3,4-dihydroxyphenyl)propanoate;
2-Acetyloxyethyl (2S)-2-amino-3-(3,4-dihydroxyphenyl)propanoate;
(2R)-2-Phenylcarbonyloxypropyl (2S)-2-amino-3-(3,4-dihydroxyphenyl)propanoate;
(2S)-2-Phenylcarbonyloxypropyl (2S)-2-amino-3-(3,4-dihydroxyphenyl)propanoate;
(2R)-2-(4-Fluorophenylcarbonyloxy)propyl (2S)-2-amino-3-(3,4-dihydroxyphenyl)propanoate;
(2S)-2-(4-Fluorophenylcarbonyloxy)propyl (2S)-2-amino-3-(3,4-dihydroxyphenyl)propanoate;
(1R)-1-Methyl-2-phenylcarbonyloxyethyl (2S)-2-amino-3-(3,4-dihydroxyphenyl)propanoate;
(1S)-1-Methyl-2-phenylcarbonyloxyethyl (2S)-2-amino-3-(3,4-dihydroxyphenyl)propanoate;
(1R)-1-Methyl-2-(4-fluorophenylcarbonyloxy)ethyl (2S)-2-amino-3-(3,4-dihydroxyphenyl)propanoate;
(1S)-1-Methyl-2-(4-fluorophenylcarbonyloxy)ethyl (2S)-2-amino-3-(3,4-dihydroxyphenyl)propanoate;
(1R,2R)-1-Methyl-2-phenylcarbonyloxypropyl (2S)-2-amino-3-(3,4-dihydroxyphenyl)propanoate;
(1S,2S)-1-Methyl-2-phenylcarbonyloxypropyl (2S)-2-amino-3-(3,4-dihydroxyphenyl)propanoate;
(1R,2R)-1-Methyl-2-(4-fluorophenylcarbonyloxy)propyl (2S)-2-amino-3-(3,4-dihydroxyphenyl)propanoate;
(1S,2S)-1-Methyl-2-(4-fluorophenylcarbonyloxy)propyl (2S)-2-amino-3-(3,4-dihydroxyphenyl)propanoate;
3-(4-Methoxyphenylcarbonyloxy)propyl (2S)-2-amino-3-(3,4-dihydroxyphenyl)propanoate;
3-(2-Hydroxyphenylcarbonyloxy)propyl (2S)-2-amino-3-(3,4-dihydroxyphenyl)propanoate;
3-(4-Hydroxyphenylcarbonyloxy)propyl (2S)-2-amino-3-(3,4-dihydroxyphenyl)propanoate;
2-Hydroxy-3-phenylcarbonyloxypropyl (2S)-2-amino-3-(3,4-dihydroxyphenyl)propanoate;
(2R)-2-(2-Hydroxyphenylcarbonyloxy)propyl (2S)-2-amino-3-(3,4-dihydroxyphenyl)propanoate;
(2R)-2-(4-Hydroxyphenylcarbonyloxy)propyl (2S)-2-amino-3-(3,4-dihydroxyphenyl)propanoate;
(2R)-2-(4-Methoxyphenylcarbonyloxy)propyl (2S)-2-amino-3-(3,4-dihydroxyphenyl)propanoate;
2-[(2-Hydroxyphenyl)carbonylamino]ethyl (2S)-2-amino-3-(3,4-dihydroxyphenyl)propanoate;
2(R)-(3-Pyridylcarbonyloxy)propyl (2S)-2-amino-3-(3,4-dihydroxyphenyl)propanoate;
2(S)-(3-Pyridylcarbonyloxy)propyl (2S)-2-amino-3-(3,4-dihydroxyphenyl)propanoate;
2(R)-(4-Pyridylcarbonyloxy)propyl (2S)-2-amino-3-(3,4-dihydroxyphenyl)propanoate;
2(S)-(4-Pyridylcarbonyloxy)propyl (2S)-2-amino-3-(3,4-dihydroxyphenyl)propanoate;
2(R)-(2-Ethoxy-3-pyridylcarbonyloxy)propyl (2S)-2-amino-3-(3,4-dihydroxyphenyl)propanoate;
2(S)-(2-Ethoxy-3-pyridylcarbonyloxy)propyl (2S)-2-amino-3-(3,4-dihydroxyphenyl)propanoate;
2(R)-(2-Methyl-5-pyridylcarbonyloxy)propyl (2S)-2-amino-3-(3,4-dihydroxyphenyl)propanoate; and
2(S)-(2-Methyl-5-pyridylcarbonyloxy)propyl (2S)-2-amino-3-(3,4-dihydroxyphenyl)propanoate; and
pharmaceutically acceptable salts thereof.

26. A compound according to claim 1, wherein the compound is selected from:
(2R)-2-Phenylcarbonyloxypropyl (2S)-2-amino-3-(3,4-dihydroxyphenyl)propanoate;
(2R)-2-(4-Methoxyphenylcarbonyloxy)propyl (2S)-2-amino-3-(3,4-dihydroxyphenyl)propanoate;
(2R)-2-(4-Hydroxyphenylcarbonyloxy)propyl (2S)-2-amino-3-(3,4-dihydroxyphenyl)propanoate;
(2R)-2-(2-Hydroxyphenylcarbonyloxy)propyl (2S)-2-amino-3-(3,4-dihydroxyphenyl)propanoate;
2-Hydroxy-3-phenylcarbonyloxypropyl (2S)-2-amino-3-(3,4-dihydroxyphenyl)propanoate;
3-(4-Hydroxyphenylcarbonyloxy)propyl (2S)-2-amino-3-(3,4-dihydroxyphenyl)propanoate;
3-(4-Methoxyphenylcarbonyloxy)propyl (2S)-2-amino-3-(3,4-dihydroxyphenyl)propanoate;
(1R,2R)-1-Methyl-2-(4-fluorophenylcarbonyloxy)propyl (2S)-2-amino-3-(3,4-dihydroxyphenyl)propanoate;
(1S,2S)-1-Methyl-2-phenylcarbonyloxypropyl (2S)-2-amino-3-(3,4-dihydroxyphenyl)propanoate;
(1R)-1-Methyl-2-(4-fluorophenylcarbonyloxy) ethyl (2S)-2-amino-3-(3,4-dihydroxyphenyl)propanoate;
(1S)-1-Methyl-2-phenylcarbonyloxyethyl (2S)-2-amino-3-(3,4-dihydroxyphenyl)propanoate;
(2S)-2-(4-Fluorophenylcarbonyloxy)propyl (2S)-2-amino-3-(3,4-dihydroxyphenyl)propanoate;
(2R)-2-(4-Fluorophenylcarbonyloxy)propyl (2S)-2-amino-3-(3,4-dihydroxyphenyl)propanoate;
(2S)-2-Phenylcarbonyloxypropyl (2S)-2-amino-3-(3,4-dihydroxyphenyl)propanoate;
2-Phenylcarbonyloxyethyl (2S)-2-amino-3-(3,4-dihydroxyphenyl)propanoate;
(1R)-1-Methyl-2-phenylcarbonyloxyethyl (2S)-2-amino-3-(3,4-dihydroxyphenyl)propanoate hydrochloride; and
pharmaceutically acceptable salts thereof.

27. The compound of claim 25 or 26, wherein the pharmaceutically acceptable salt is the hydrochloride salt.

28. A pharmaceutical composition comprising at least one pharmaceutically acceptable excipient, and a therapeutically effective amount of at least one compound of Formula (I) according to claim 1.

29. A pharmaceutical composition according to claim 28, further comprising at least one decarboxylase inhibitor.

30. A pharmaceutical composition according to claim 29, wherein the at least one decarboxylase inhibitor is selected from carbidopa, a carbidopa prodrug, benserazide, and a benserazide prodrug.

31. A pharmaceutical composition according to claim 28, further comprising at least one catechol O-methyltransferase inhibitor.

32. A pharmaceutical composition according to claim 31, wherein the at least one catechol O-methyltransferase inhibitor is selected from entacapone, an entacapone prodrug, tolcapone, and a tolcapone prodrug.

33. A pharmaceutical composition according to claim 28, wherein the pharmaceutical composition is formulated for oral administration.

34. A pharmaceutical composition according to claim 28, wherein the pharmaceutical composition is a sustained release formulation.

35. A pharmaceutical composition according to claim 28, wherein the at least one compound is present in an amount effective for the treatment in a patient of Parkinson's disease.

36. A pharmaceutical composition according to claim 28, wherein the at least one compound is present in an amount effective for the treatment in a patient of a disease selected from depression, attention deficit disorder; schizophrenia, manic depression, cognitive impairment disorders, restless legs syndrome, periodic limb movement disorders, tardive dyskinesia, Huntington's disease, Tourette's syndrome, hypertension, addictive disorders, congestive heart failure, and excessive daytime sleepiness.

37. A compound according to claim 1, which when administered in the colon of a patient is taken up at a rate to achieve a bioavailability of levodopa at least 2-fold greater than the bioavailability of levodopa acheived when levodopa is administered in the colon of the patient.

38. A compound according to claim 1, wherein each $R^1$ and $R^2$ is independently selected from hydrogen, alkanyl, substituted alkanyl, arylalkanyl, substituted arylalkanyl, cycloalkanyl, substituted cycloalkanyl, cycloheteroalkanyl, substituted cycloheteroalkanyl, halo, heteroalkanyl, substituted heteroalkanyl, heteroarylalkanyl, and substituted heteroarylalkanyl.

39. A compound according to claim 1, wherein each $R^1$ and $R^2$ is independently selected from hydrogen, methyl, ethyl, propyl, isopropyl, butyl, isobutyl, sec-butyl, tert-butyl, cyclopropyl, cyclobutyl, cyclopentyl, cylohexyl, and benzyl.

40. A compound according to claim 1, wherein each $R^1$ and $R^2$ is independently selected from hydrogen, alkanyl, substituted alkanyl, arylalkanyl, aryl, substituted aryl, heteroaryl, and substituted heteroaryl.

41. A compound according to claim 1, wherein each $R^1$ and $R^2$ is independently selected from hydrogen, —OH, $C_{1-6}$ alkyl, and substituted $C_{1-6}$ alkyl.

42. A compound of claim 22, wherein the compound is selected from:
- (2R)-2-Phenylcarbonyloxypropyl (2S)-2-amino-3-(3,4-dihydroxyphenyl)propanoate;
- (2S)-2-Phenylcarbonyloxypropyl (2S)-2-amino-3-(3,4-dihydroxyphenyl)propanoate;
- a pharmaceutically acceptable salt of any of the foregoing, and a combination of any of the foregoing.

43. A compound of claim 22, wherein the compound is selected from:
- (1R)-1-Methyl-2-phenylcarbonyloxyethyl (2S)-2-amino-3-(3,4-dihydroxyphenyl)propanoate;
- (1S)-1-Methyl-2-phenylcarbonyloxyethyl (2S)-2-amino-3-(3,4-dihydroxyphenyl)propanoate;
- a pharmaceutically acceptable salt of any of the foregoing, and a combination of any of the foregoing.

44. The compound of any one of claims 42 and 43, wherein the pharmaceutically acceptable salt is selected from the hydrochloride salt.

45. The compound of any one of claims 23 and 24, wherein $R^{11}$ is selected from monosubstituted fluoro, chloro, bromo, methyl, and methoxy.

* * * * *

UNITED STATES PATENT AND TRADEMARK OFFICE
CERTIFICATE OF CORRECTION

PATENT NO. : 7,342,131 B2  
APPLICATION NO. : 11/145159  
DATED : March 11, 2008  
INVENTOR(S) : Jia-Ning Xiang et al.

It is certified that error appears in the above-identified patent and that said Letters Patent is hereby corrected as shown below:

On the face of the Patent

"(*) Notice: Subject to any disclaimer, the term of this patent is extended or adjusted under 35 U.S.C. 154(b) by 95 days"

should read:

--(*) Notice: Subject to any disclaimer, the term of this patent is extended or adjusted under 35 U.S.C. 154(b) by 94 days--.

In claim 13, column 47, line 42, "and are" should read --and $R^4$ are--.

In claim 22, column 48, line 39, "$R^1$ is selected" should read --each $R^1$ is independently selected--.

In claim 23, column 48, lines 51-60,

" 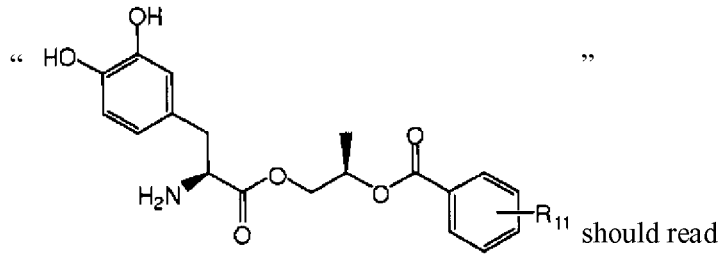 should read

-- 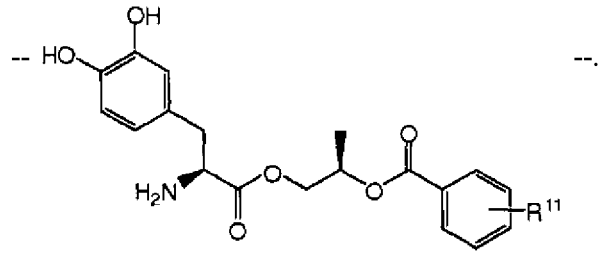 --.

UNITED STATES PATENT AND TRADEMARK OFFICE
CERTIFICATE OF CORRECTION

PATENT NO. : 7,342,131 B2
APPLICATION NO. : 11/145159
DATED : March 11, 2008
INVENTOR(S) : Jia-Ning Xiang et al.

It is certified that error appears in the above-identified patent and that said Letters Patent is hereby corrected as shown below:

In claim 24, column 49, lines 1-12,

" 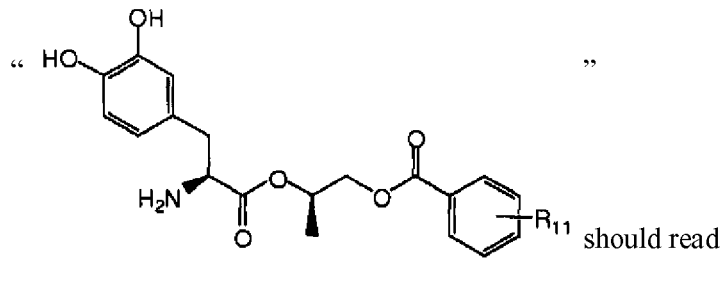 " should read

-- 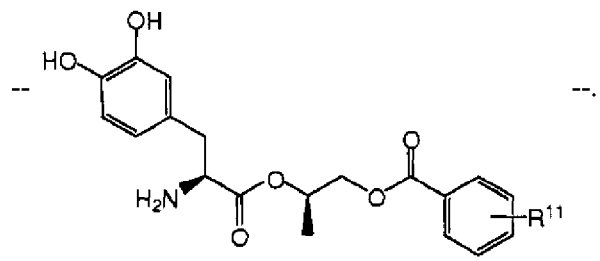 --.

In claim 36, column 51, line 21, "disorder;" should read --disorder,--.

In claim 37, column 51, line 30, "acheived" should read --achieved--.

Signed and Sealed this

Seventh Day of July, 2009

JOHN DOLL
*Acting Director of the United States Patent and Trademark Office*